United States Patent
Imran

(10) Patent No.: US 9,795,296 B2
(45) Date of Patent: Oct. 24, 2017

(54) MOUTHPIECE FOR MEASUREMENT OF BIOMETRIC DATA OF A DIVER AND UNDERWATER COMMUNICATION

(75) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 474 days.

(21) Appl. No.: 13/457,456

(22) Filed: Apr. 26, 2012

(65) Prior Publication Data
US 2013/0116512 A1 May 9, 2013

Related U.S. Application Data

(60) Provisional application No. 61/479,265, filed on Apr. 26, 2011.

(51) Int. Cl.
*A61B 5/1455* (2006.01)
*A61B 5/00* (2006.01)
(Continued)

(52) U.S. Cl.
CPC .......... *A61B 5/0002* (2013.01); *A61B 5/0816* (2013.01); *A61B 5/14551* (2013.01);
(Continued)

(58) Field of Classification Search
CPC .............. A61B 5/1455; A61B 5/14551; A61B 5/14552; A61B 5/14553; A61B 5/0059;
(Continued)

(56) References Cited

U.S. PATENT DOCUMENTS

| | | | | |
|---|---|---|---|---|
| 4,653,498 A | * | 3/1987 | New et al. | 600/324 |
| 5,040,539 A | * | 8/1991 | Schmitt | A61B 5/0088 600/340 |
| 5,069,214 A | * | 12/1991 | Samaras et al. | 600/323 |
| 5,579,284 A | | 11/1996 | May | |

(Continued)

FOREIGN PATENT DOCUMENTS

EP          2 075 189 A1     7/2009

OTHER PUBLICATIONS

International Search Report, Written Opinion and Notice mailed Nov. 30, 2012 in PCT Application PCT/US2012/035310.

*Primary Examiner* — Eric Winakur
*Assistant Examiner* — Chu Chuan (JJ) Liu
(74) *Attorney, Agent, or Firm* — Mahamedi IP Law LLP; Joel Harris

(57) ABSTRACT

Embodiments of the invention provide a system, apparatus and methods for measurement of biometric data of a diver. In many embodiments, the system includes a mouthpiece having a sensor device comprising a light emitter and detector configured to emit and detect light at a wavelength having an absorbance correlated with a level of a blood gas saturation e.g., oxygen, nitrogen, $CO_2$. The emitter is positioned to emit light onto oral tissue of the diver and the detector positioned to detect light which is received from the oral tissue either by transmittance of light through the oral tissue or by reflection of light from the tissue. The target oral tissue can include one or both of gum or buccal tissue. Such embodiments allow data to be collected without having to wear additional sensors or measurement devices and allow for measurement of blood gas levels as the diver breaths through their mouthpiece.

35 Claims, 23 Drawing Sheets

(51) Int. Cl.
*A61B 5/08* (2006.01)
*B63C 11/26* (2006.01)
*B63C 11/18* (2006.01)

(52) U.S. Cl.
CPC ............ *A61B 5/682* (2013.01); *A61B 5/6803* (2013.01); *B63C 11/26* (2013.01); *A61B 2562/0204* (2013.01); *A61B 2562/0238* (2013.01); *B63C 11/186* (2013.01)

(58) Field of Classification Search
CPC . A61B 5/14532; A61B 5/0088; A61B 5/0205; A61B 5/0816; A61B 5/145; A61B 5/6803; A61B 5/682
USPC ....... 600/310, 322, 323, 324, 326, 333, 340, 600/344, 473, 476; 356/41
See application file for complete search history.

(56) References Cited

U.S. PATENT DOCUMENTS

| | | | |
|---|---|---|---|
| 6,402,690 B1* | 6/2002 | Rhee et al. .................. | 600/323 |
| 2003/0028085 A1* | 2/2003 | Al-Ali .................. | A61B 5/1455 |
| | | | 600/323 |
| 2005/0113654 A1* | 5/2005 | Weber ..................... | A61B 5/01 |
| | | | 600/309 |
| 2007/0027375 A1* | 2/2007 | Melker et al. .............. | 600/340 |
| 2008/0037018 A1* | 2/2008 | Hoffmann ............ | A61B 5/0088 |
| | | | 600/300 |
| 2010/0006098 A1 | 1/2010 | McGinnis et al. | |
| 2010/0317970 A1 | 12/2010 | Gu et al. | |
| 2012/0062716 A1* | 3/2012 | Dillon .................. | A61C 9/006 |
| | | | 348/66 |

\* cited by examiner

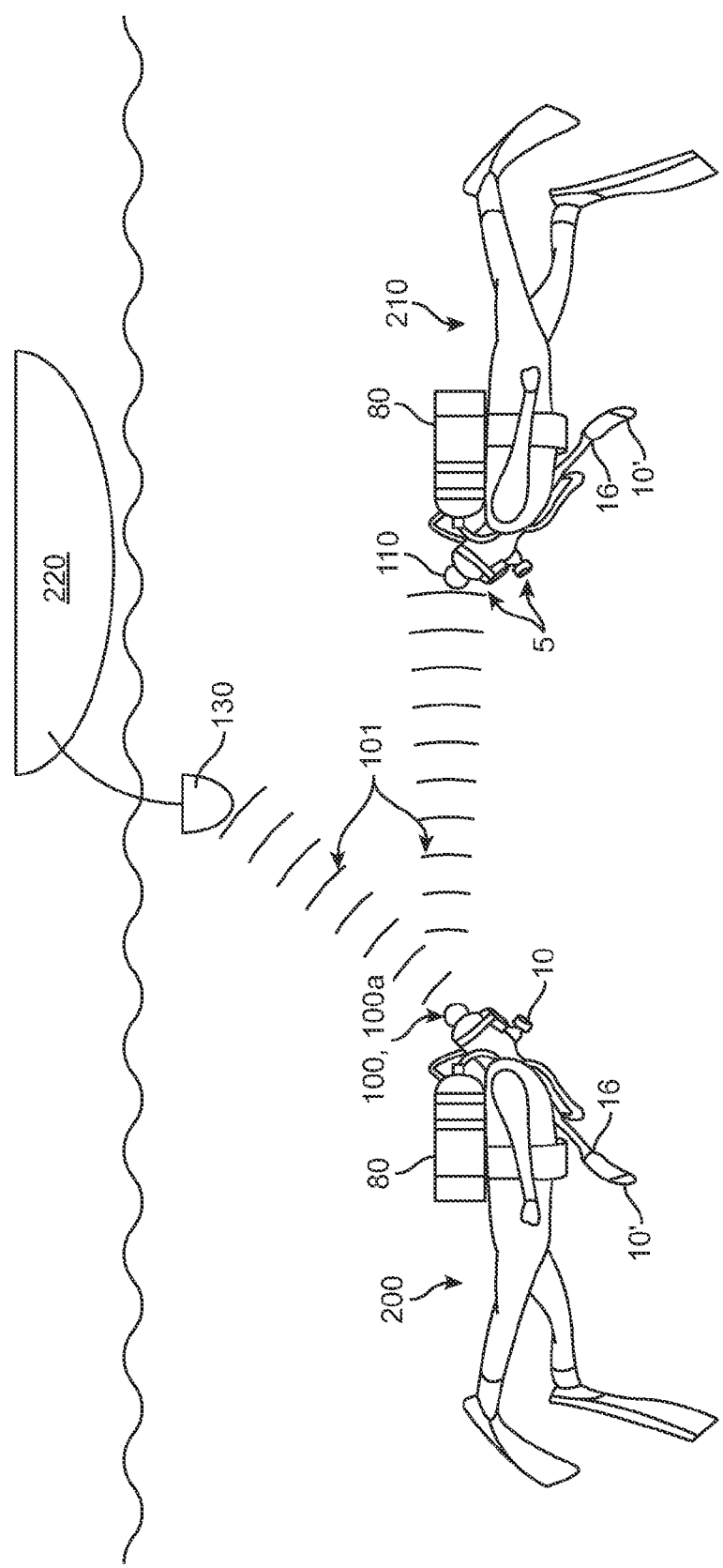

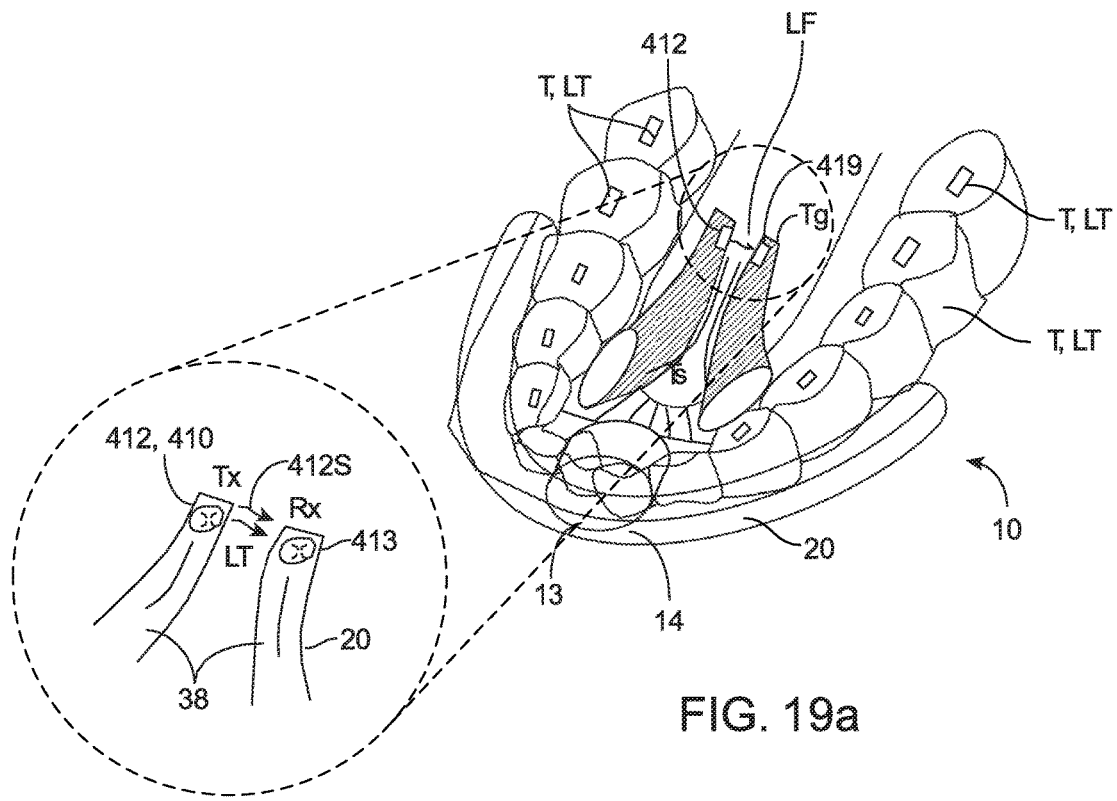
FIG. 19a
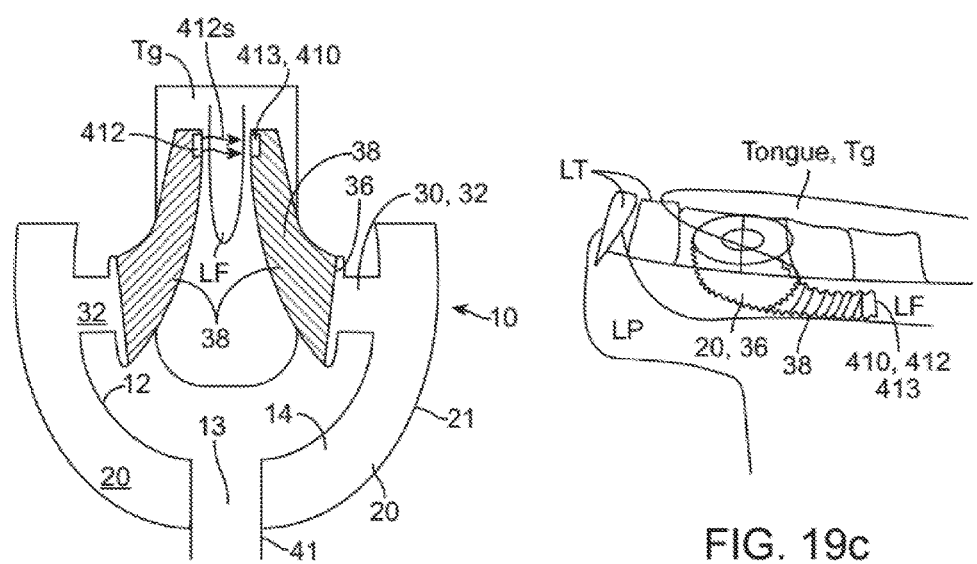
FIG. 19b
FIG. 19c

MOUTHPIECE FOR MEASUREMENT OF BIOMETRIC DATA OF A DIVER AND UNDERWATER COMMUNICATION

RELATED APPLICATIONS

This application claims priority to U.S. Provisional Patent Application No. 61/479,265 filed Apr. 26, 2011, entitled "MOUTHPIECE FOR MEASUREMENT OF BIOMETRIC DATA OF A DIVER AND UNDERWATER COMMUNICATION", which is fully incorporated by reference for all purposes. This application also claims priority to U.S. patent application Ser. No. 13/237,912, filed Sep. 20, 2011, entitled, "DEVICE, SYSTEM AND METHOD FOR MONITORING AND COMMUNICATING BIOMETRIC DATA OF A DIVER", which is fully incorporated by reference for all purposes This application is related to U.S. patent application Ser. No. 13/231,881, filed Sep. 13, 2011, entitled, "SELF-PROPELLED BUOY FOR MONITORING UNDERWATER OBJECTS"; U.S. patent application Ser. No. 13/352,249 filed Jan. 17, 2012, entitled, "APPARATUS, SYSTEM AND METHOD FOR UNDERWATER VOICE COMMUNICATION BY A DIVER"; and U.S. patent application Ser. No. 13/398,718, filed Feb. 16, 2012, entitled "APPARATUS, SYSTEM AND METHOD FOR UNDERWATER SIGNALING OF AUDIO MESSAGES TO A DIVER"; all of the aforementioned applications are hereby incorporated in their entirety by reference herein for all purposes.

FIELD OF THE INVENTION

Embodiments described herein relate to a system for underwater voice communication. More specifically, embodiments described herein relate to an apparatus, system and method for underwater communication by a diver, such as a SCUBA (Self Contained Underwater Breathing Apparatus) or skin diver.

BACKGROUND

Since the early days of SCUBA diving with Jacque Cousteau, communication between SCUBA divers has been an issue. This is due to the fact that i) the use of the SCUBA breathing apparatus (including a mouth piece worn by the diver precludes voice direct voice communication, and ii) because of risks of the underwater environment, divers have a critical need to communicate a variety of safety related messages to their fellow divers, e.g., communicating the amount of air they have remaining (a maxim of diving is to never dive alone, but instead always go with at least one other diver known as a "dive buddy"). As a result, a series of hand signs have been developed but these only cover a very limited number of messages and cannot quickly get the other divers attention in critical situations. Various underwater graphical display devices have also been developed, but these have the same limitation. These devices which are worn on the diver's wrist or arm require the diver to divert his or her attention from what they are doing to look at the display. Typically, divers dive with their head up to see where they are going and their arms at their sides to reduce water resistance. So, the diver's natural diving position is not conducive to monitoring a visual alert on their wrist or elsewhere (e.g., arm or waist). This is even true for visual alerts on the divers face mask since the diver attention is more focused on what is in front of them and not their face mask.

Acoustic alarm systems have been developed but they are not voice based and can only communicate a limited number of messages which require the diver to understand an alarm code. Also, none of these devices provide for communication between divers and a surface craft such as the dive boat (the boat which supports the divers). Further none of these devices provides for communication between divers who are not in very close proximity. What is needed is an approach allowing for voice communication between divers while they are underwater as for voice communication between divers and a surface craft.

BRIEF DESCRIPTION OF THE INVENTION

Embodiments of the invention provide a wearable mouthpiece and system for measurement and communication of biometric data of a diver and/or for underwater voice communication by the diver to other divers and/or surface ships. Embodiments also provide underwater voice communication between a diver and an underwater electronic device which generates voice messages for the diver. In many embodiments, the system includes a dive computer or like device having the ability to generate audio messages, a mouthpiece having an acoustic transducer that conducts sound via conduction through the diver's teeth and skull to the cochlea, so as to allow the diver to hear the audio messages and other sounds, and a microphone for sensing the diver's voice. The mouthpiece is adapted to be easily attached to portions of a SCUBA or other underwater breathing apparatus. It may also be attached to or integrated with a snorkel or similar apparatus. One or both of the mouthpiece and the dive computer may include circuitry for amplifying higher frequency components of the audio messages or other sounds to account for reduced level of conduction of such frequencies by bone.

Embodiments of the invention allow the diver to speak and have two way voice communication with other divers and surface ships without having to remove their mouthpiece and without having any other specialized equipment. Embodiments of the invention also allow the diver to hear audio messages such as acoustic alarms, voice messages and prompts from a portable dive computer or other underwater electronic device. In use, such embodiments allow the diver to perform various tasks while receiving a variety of information including voice prompts and commands without having to look at a display or gauge. This enables the divers to stay focused on their task and/or their underwater environment, thereby improving the divers' safety and diving experience. Still other embodiments of the invention allow divers to hear music, radio or other audio input while they are underwater. Other embodiments provide a diver with an acoustic input of sounds from the body of water in which he or she is diving to allow the diver to hear the sounds of underwater marine life as well as the sounds of surface crafts.

In one embodiment, the invention provides a mouthpiece apparatus for measuring biometric data of a diver such as oxygen or other blood gas saturation level. The apparatus comprises a flexible mouthpiece having an exterior coupling element for coupling to an air hose or other conduit of a SCUBA (or other underwater breathing apparatus) and an interior portion coupled to the coupling element and worn in the diver's mouth. The coupling element may be coupled directly to the air hose or to a fitting on the air hose. The coupling element and interior portion can include a lumen for the passage of respired air by the diver. The interior portion has a curved shaped corresponding to a shape of the diver's mouth and has attached right and left bite structures. The bite structures include upper and lower surfaces for engaging a bite surface of the diver's upper and lower teeth. One or both of the bite structures may include a retaining flange (e.g., which can be perpendicular) to a bite surface of the bite structure for retaining the mouthpiece in the diver's mouth. The bite structure may also include a tongue flap or flange which lies partially underneath the back portion of the tongue. The tongue flap can include at least one pair of emitters and detectors configured to emit and detect light at a wave length having an correlated with a level of blood gas saturation as is described above.

The mouthpiece may also include a sensor device comprising a light emitter and a light detector configured to emit and detect light at a wave length having an absorbance correlated to a level of a blood gas saturation. In many embodiments, the emitted light is selected to measure blood oxygen saturation using a ratio of the intensity of the emitted light to the detected light. The emitter is positioned to emit light onto oral tissue of the diver and the detector is positioned to detect light which is received from the oral tissue either by transmittance of light through the oral tissue or by reflection of light from the tissue. The target oral tissue used for the blood gas measurements can include one or both of the divers gum tissue or the buccal (e.g., check tissue). Accordingly, the emitter and detector may be positioned in a number of locations in or on the mouthpiece to make such measurements including the interior surface of the mouthpiece as well as the left or right bite structure, the retaining flange, and in a preferred embodiment on the tongue flap. They may also be positioned on the surface of the mouthpiece or embedded within the mouthpiece. In other embodiments, the emitter and detector may be recessed within the mouthpiece while still having direct exposure to the diver's oral tissue (cheek or gum) or partially covered by an optically transparent layer used as moisture guard. According to many embodiments, the mouthpiece is sufficiently flexible to conform to the contour of the diver's oral tissue (e.g., the cheek and/or gum) and also sufficiently resilient to maintain contact with the oral tissue when that tissue moves due to movement of the divers mouth, jaw, teeth, etc. Owing to the flexibility and resilience of the mouthpiece and the positioning of the emitter and detector, the mouthpiece is able to maintain substantial physical and/or optical contact between the diver's oral tissue and the emitter and detector during movement of one or more of the divers mouth, jaw, teeth, cheek, etc. In use, these and related embodiments allow the mouthpiece to maintain such physical and/or optical contact so as to be able to continue to make blood gas measurements when the diver inhales, exhales, cough, speaks or makes any vocal sound and to do so without impeding the diver's breathing. In use, such embodiments also allow for the measurement of blood oxygen or other blood gas level without the diver having to wear or otherwise be encumbered by any other sensor device.

In some embodiments, an acoustic transducer is positioned on the top surface of at least one of the left or right bite structures of the mouthpiece. The acoustic transducer is configured to transduce an electrical signal input (e.g., from another communication device) into an acoustic output and to acoustically couple to the diver's upper teeth. The acoustic transducer may conduct the acoustic output from the diver's upper teeth through the skull to generate audible sound in at least one of the diver's ears when the diver is wearing the mouthpiece. The sounds may be used to communicate to the diver various biometric measurements made, for example, by the mouthpiece (e.g., blood oxygen saturation, pulse, etc.) as well as when those measurements cross a threshold (e.g., when blood oxygen levels fall below e.g., 95%). Typically, the acoustic transducer is positioned to engage the upper (e.g., maxillary) back teeth of the diver's mouth, but may positioned to engage any tooth or group of teeth in the diver's mouth. Also, the transducer properties can be tuned or otherwise adjusted according to a diver's preference or for efficiency and/or effectiveness. A microphone may also be positioned in or on the mouthpiece for detecting the diver's voice and for generating an electrical output signal when the diver is wearing the mouthpiece. The microphone may be recessed or otherwise positioned to reduce breathing sounds. This microphone output can be sent to an underwater communication device for underwater transmission to another diver(s) or to a surface ship. In other embodiments, the communication device may correspond to an ultrasonic or other acoustical transmission device which transduces the electrical output signal into an acoustic signal so that it may be transmitted by the acoustical transmission device. Also, in various embodiments, one or both of the communication device or microphone may include a filter (e.g., high pass, low pass, etc.) for filtering out breath and related sounds of the diver from his or her spoken words.

In an exemplary embodiment of using the invention, the diver attaches an embodiment of the mouthpiece to a fitting on a regulator or other component of his or her SCUBA gear. For embodiments having electrical couplings on the mouthpiece, the diver may then connect them to the underwater communication device. He or she may perform a few quick tests to assure that the communication system is working. Such tests can include putting in the mouthpiece and saying some test phrases (e.g., "testing 1, 2, 3," etc.) while looking at a display on or coupled to the communication device to assure that a signal from the microphone is being received by the communication device. The test for the acoustic transducer can comprise putting in the mouthpiece and pressing a test signal button on the communication device which then sends a test signal to the acoustical transducer, which converts the electrical signal to an audio signal conducted through his teeth and skull, and which the diver then listens for. For either test, the diver can move the mouthpiece around in his or her mouth to find a position of the mouthpiece in his or her mouth which yields the best audio input and/or electrical output signal from the microphone. The diver may perform a similar procedure for embodiments of the mouthpiece used in a snorkel. Having found that position, the diver may select a particular acoustic frequency or range of frequencies (e.g., akin to a channel) to use for input (hearing) and output (verbal speech). The diver may choose to use the system underwater for voice communication with other divers as well as surface ship. Depending upon the frequencies available, the diver may then select/assign a distinct acoustic frequency or frequency range for a particular diver as well as for a surface craft. In many embodiments, the system will allow for separate frequency and/or frequency range to minimize cross talk from diver to diver as well as diver to surface ship communication. These and other aspects, embodiments and features are described in detail in the body of specification.

BRIEF DESCRIPTION OF THE DRAWINGS

FIG. 1 is a schematic view of an embodiment of an underwater voice communication system for a diver.

FIG. 19a is a perspective view of an embodiment of a mouthpiece including a sensor device for measuring blood oxygen using absorbance oximetry where the mouthpiece includes a flap for positioning of the emitter and detector beneath the tongue.

FIG. 19b is a bottom view of the embodiment of FIG. 19a showing the positioning of flaps underneath the tongue and on either side of the Lingual Frenulum.

FIG. 19c is a lateral view of the embodiment of FIG. 19a showing the positioning of the flap on either side of the tongue and Lingual Frenulum.

DETAILED DESCRIPTION OF THE INVENTION

Figure 1A:
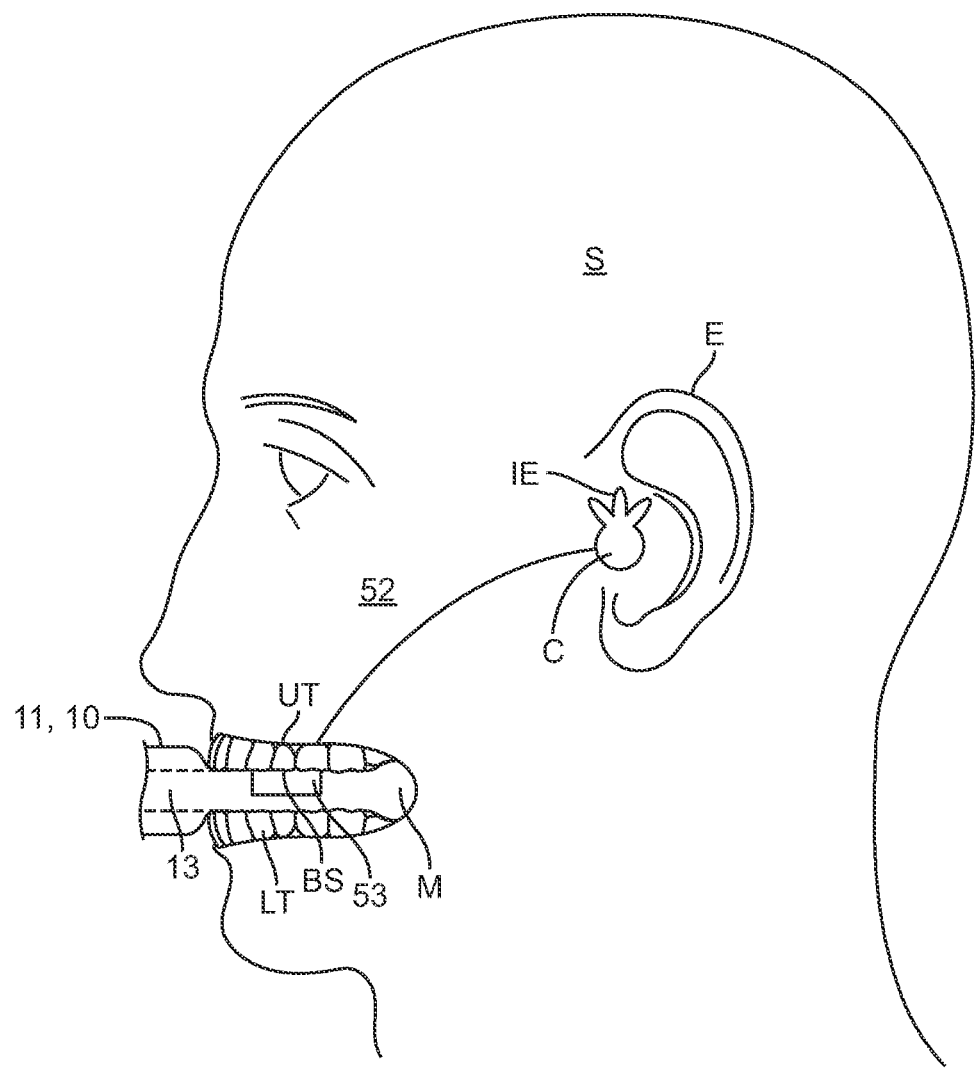
FIG. 1a shows an embodiment of a voice communication mouthpiece apparatus worn in the mouth and its use in the conduction of sound to the inner ear through the skull.
Figure 2:
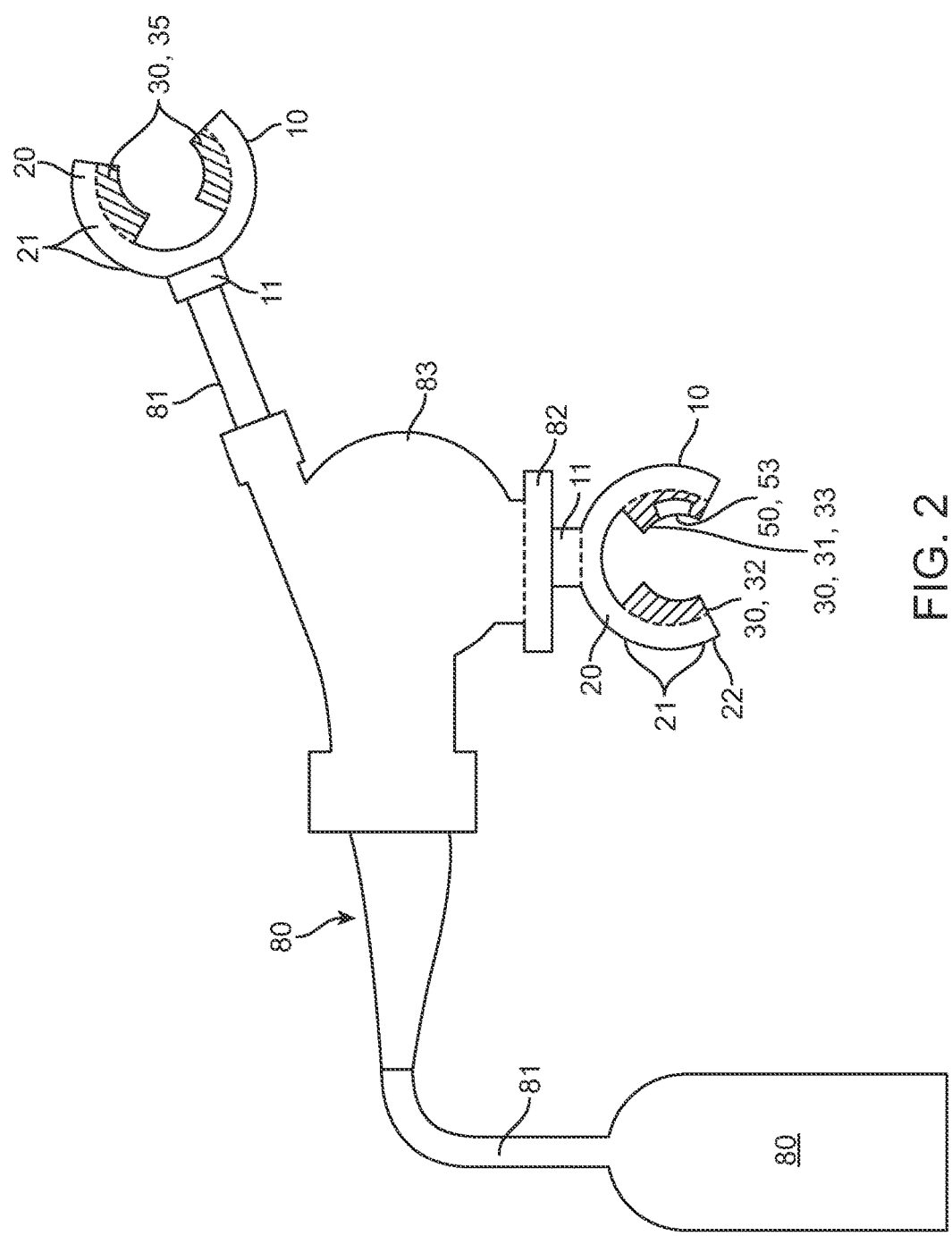
FIG. 2 is a lateral view illustrating embodiments of the mouthpiece coupled to an underwater breathing apparatus such as a SCUBA.
Figure 3:
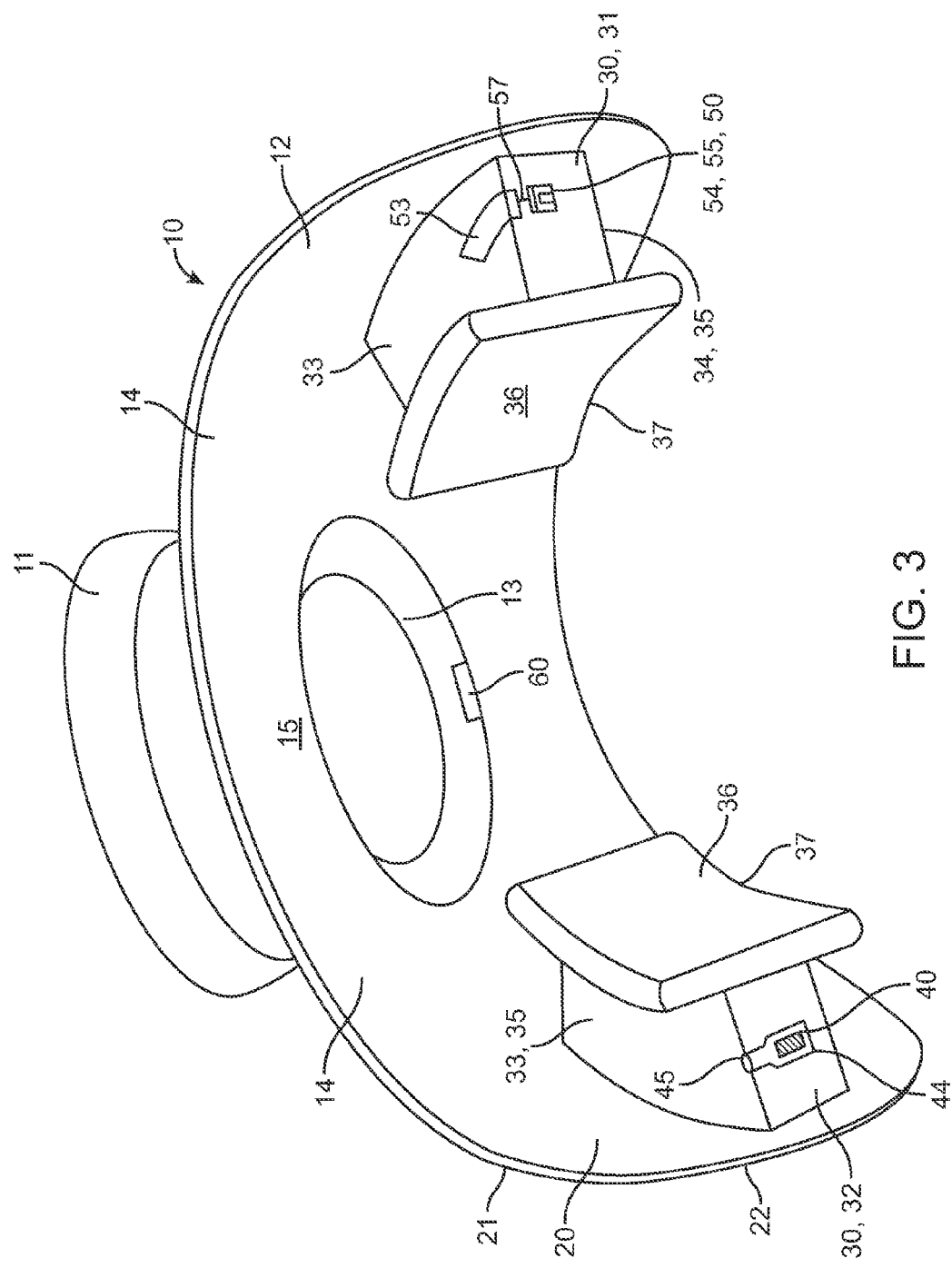
FIG. 3 is a perspective view showing various features of an embodiment of the mouthpiece.
Figure 4:
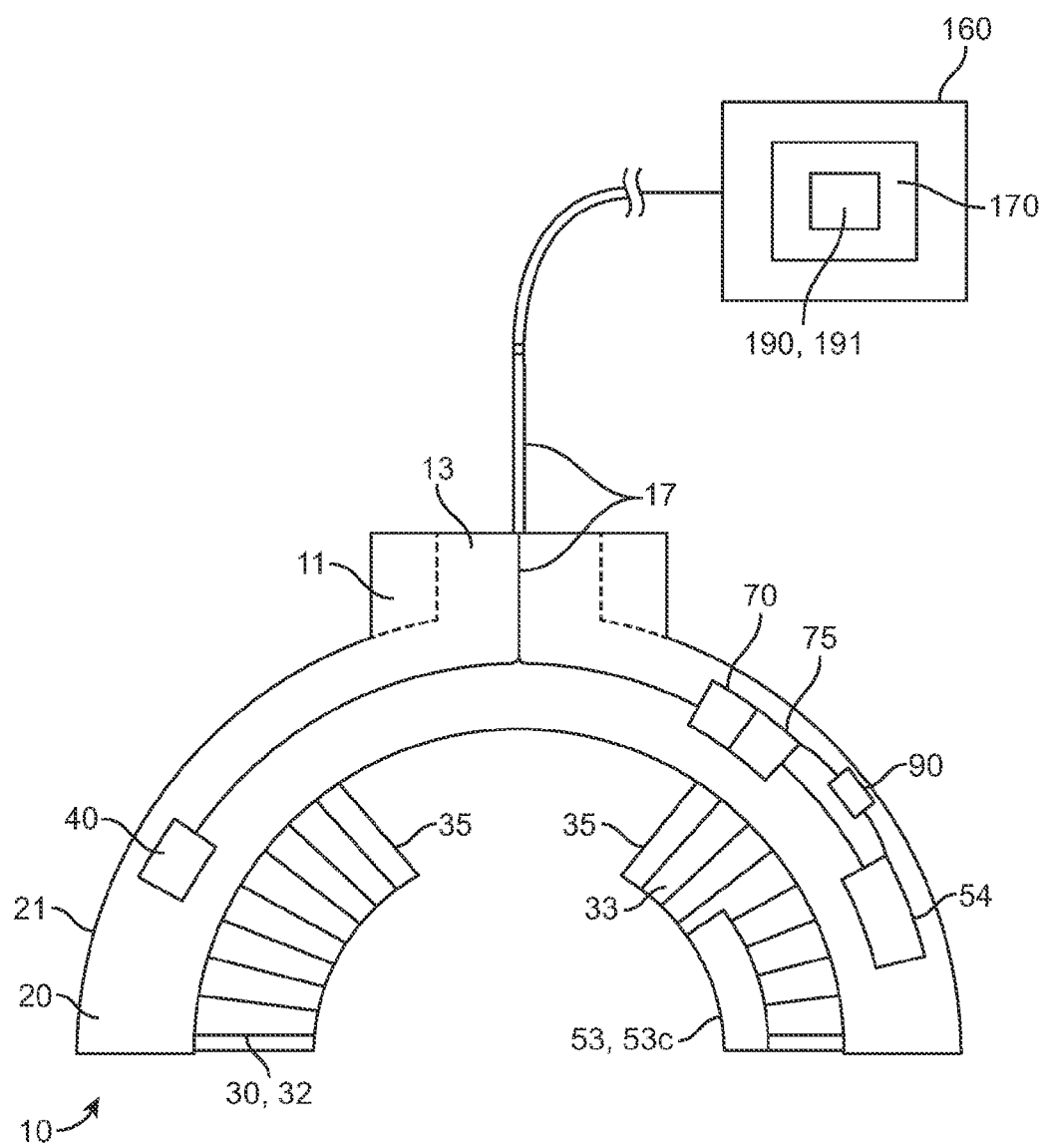
FIG. 4 is a lateral view showing an embodiment of the mouthpiece having an electrical connection means such as a wire for coupling to PWE devices such as a dive computer.
Figure 5A:
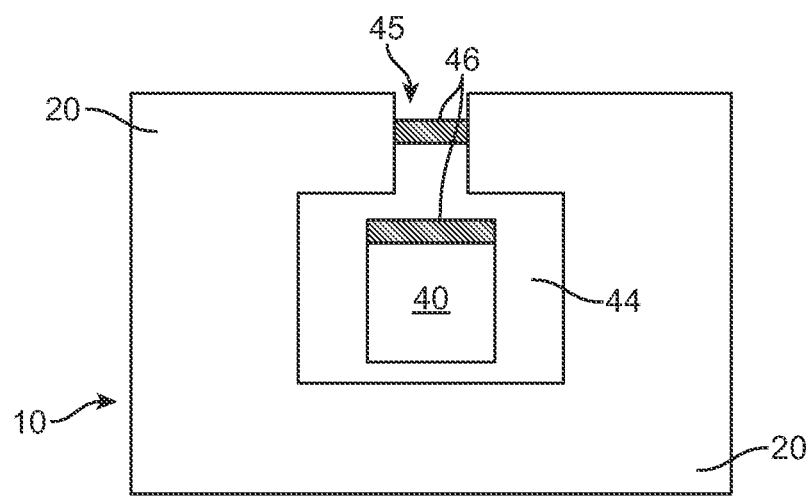
FIG. 5a is a side cut-away view showing an embodiment of the mouthpiece having a cavity and a microphone positioned in the cavity.
Figure 5B:
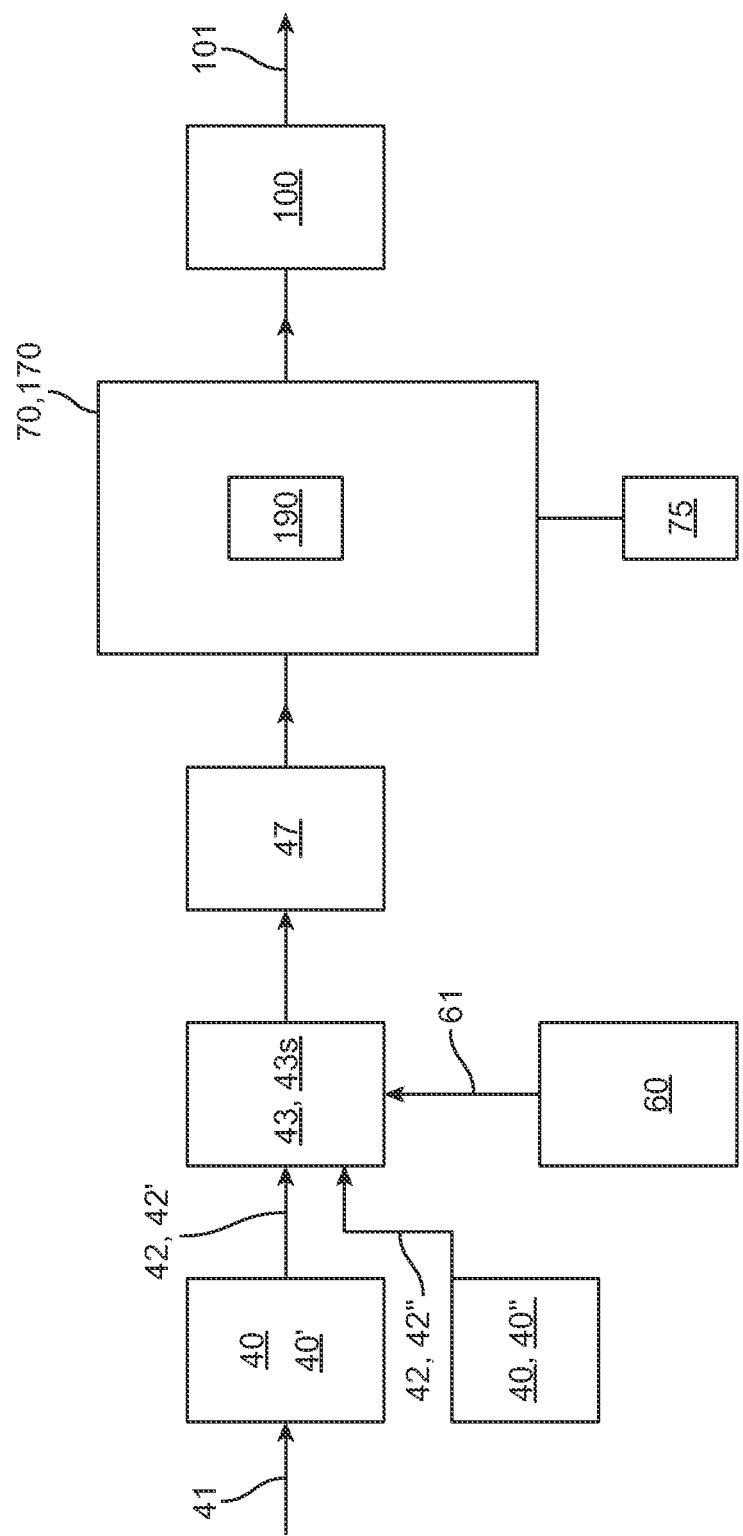
FIG. 5b is a block diagram illustrating the configuration and operation of an embodiment of the microphone.

Referring now to FIGS. 1-19, an embodiment of a communication system 5 for voice communication from a first diver 200 to one or more other divers 210 or surface ships 220 comprises a mouthpiece apparatus 10 (herein mouthpiece 10) and an underwater communication device 100. In various embodiments, communication system 5 also provides for communication of computer generated voice messages to the diver from a portable underwater device. Mouthpiece 10 is worn in the diver's mouth and is configured to attach to a regulator 82 or other fitting 83 of a SCUBA or other underwater diving apparatus 80. System 5, including mouthpiece 10, is configured to allow voice or other communication between a first underwater communication device 100 carried by diver 200 and a second underwater communication device 110 carried by other diver(s) 210 as well as between communication device 100 and a communication device 130 used by a ship 220. In one embodiment, communication device 130 can be incorporated into a buoy or array towed by ship 220. With regard to communication device 100 (and 110), it can be positioned on a variety of locations on the diver and/or on Scuba 80. In one embodiment, it may be positioned on the diver's head and can be attached using a band or strap or it may be coupled to the hood of the diver's wetsuit. In many embodiments, communication device 100 may be incorporated into a portable watertight electronic device 160 carried or worn by the diver as is described herein.

In addition to communication with another diver 210 having a separate SCUBA 80, in various embodiments, system 5 and mouthpiece 10 can also be adapted for communication with another mouthpiece 10' connected to a buddy breathing line 16 connected to same SCUBA 80 as used by diver 200 as is shown in the embodiment of FIG. 1. In such embodiments, mouthpieces 10 and 10' can be configured to both be operatively connected to the same communication device 100 or they may be configured to be directly connected to each other without the use of communication device 100. In use, such embodiments allow quick and ready communication between the diver 200 and the buddy breather without the need for any communication device or any set up procedure.

The mouthpiece 10 includes a coupling element 11, an interior portion 20 coupled to the coupling element 11, a microphone 40 and an acoustic transducer 50. Coupling element 11, couples the mouthpiece 10 to SCUBA 80. In various embodiments, coupling element 11 may be configured to couple directly to an air hose 81 of SCUBA 80 or a regulator 82 or other fitting 83 of SCUBA 80. The coupling element 11 and interior portion 20 include a lumen 13 for the passage of respired air by the diver.

One or both of the microphone 40 and the acoustic transducer 50 may be powered by a battery 90 which is incorporated into the mouthpiece 10 or coupled to the mouthpiece 10, for example, by an electrical wire 17 or other electrical connection means 17. Battery 90 may comprise various lithium buttons or other miniature batteries known in the art. Battery 90 may also be shaped to have a form factor which readily fits into mouthpiece 10. For example, in one embodiment, battery 90 may have curved shape which corresponds to the curvature of the diver's dental arches DA. Battery 90 may also be used to power a processor 70 that may also be contained in the mouthpiece 10 and described in more detail herein.

Wire(s) 17 may also be configured to couple both the microphone 40 and the transducer 50 (as well as electrical components of mouthpiece 10) to various electrical devices that are part of SCUBA 80 or are otherwise worn or carried by the diver, such as communication device 100 and/or dive computer 160. Wire(s) 17 may be insulated sufficiently to withstand depths of several hundred feet or more. A portion of the wires 17 may be embedded in the mouthpiece 10 and/or connected to the mouthpiece 10 by an electrical connector configured for underwater conditions. Wire 17 can include at least a first and second wire for connection to the microphone 40 and the acoustic transducer 50. In some embodiments, a section of wire 17 may pass through lumen 13 of coupling element 11 so as to connect to one or more electrical devices that are part of SCUBA 80 or are otherwise worn or carried by the diver. In such embodiments, wire 17 is sufficiently thin or otherwise configured so as to not interfere or impede the passage of respired air through lumen 13.

In alternative or additional embodiments, one or both of the microphone 40 and the transducer 50 may be operatively coupled to communication device 100 and/or dive computer 160 via use of a wireless communication device 95, such as an RF communication chip 95 which may be embedded in the mouthpiece 10. RF communication chip 95 may correspond to an active or passive RF transceiver and may be embedded in the mouthpiece 10. The frequency and power levels for use with such an RF communication chip 95 can be adapted for underwater use to allow communication of signals 97 between an RF communication chip 95 in the mouthpiece 10 and a corresponding chip 96 in communication device 100 and/or dive computer 160 carried by the diver. In use, such embodiments allow the diver to readily couple the mouthpiece 10 to communication device 100 and/or computer 160 without having to make any electrical connections. It also allows the diver to verify that the mouthpiece 10 is operating properly before getting into the water through the use of one or more diagnostic software modules 190 resident within dive computer 160 which can be configured to interrogate mouthpiece 10 for proper operation. In one embodiment, this may consist of the diver being prompted to speak several test phrases with the mouthpiece in place. Further in various embodiments, communication chip 95 and/or memory chip or other memory resources 75 coupled to chip 95 may contain various diver specific information (e.g., name, weight, health data, dive history, etc.) which can be signaled to dive computer 160 allowing the dive computer to uniquely identify the mouthpiece 10 as belonging to a particular diver and then upload that data into the dive computer. The process may also be facilitated by use of a processor 70, such as microprocessor 70, which controls the handshake and other communication between communication chip 95 and chip 96. Processor 70 may also contain or be coupled to memory resources 75. In particular embodiments, such a configuration can be implemented through use of an ASIC (application specific integrated circuit) containing processor 70, memory resources 75 and even battery 90.

The interior portion 20 of the mouthpiece 10 has a curved shape 21 corresponding to a shape of the diver's dental arches DA and has attached right 31 and left 32, bite structures 30. The curved shape 21 may be fabricated by taking a dental impression or image of the diver's mouth and then using that impression or image to construct a mold for making the mouthpiece and/or using stereolithography techniques known in the art. The bite structures 30 include upper 33 and lower 34 surfaces 35 (also called bite surfaces 35) for engaging a bite surface BS of the diver's teeth T, such as upper teeth, UT (also called maxillary) and lower teeth, LT. Bite structures 30 may be positioned and arranged to contact at least the back teeth of the diver, but may contact the front teeth as well (or other teeth or groups of teeth). The bite structures 30 may also be configured to be acoustically isolated from each other by fabricating all or a portion of the bite structures from various acoustically insulating materials known in the art.

In various embodiments, one or both of the bite structures 30 may include a retaining flange 36 for retaining the mouthpiece in the diver's mouth M by contacting an inside surface of the diver's teeth. Typically, flange 36 will be oriented perpendicular to bite surfaces 35, but other orientations are also contemplated (e.g., an acute angle). Also, flange 36 may have a curved shape or profile 37 which corresponds to the curvature of the diver's dental arches DA.

In various embodiments, mouthpiece 10 may be fabricated from elastomeric polymers such as silicone, polyurethane, copolymers thereof and other elastomers known in the art. The mouthpiece 10 may have a unitary construction and or may be fabricated from separate components which are joined. It may be fabricated using various methods known in the polymer processing arts, including molding and stereolithography methods. Also, molding may be done with the microphone 40 and/or acoustical transducer 50 in place, or they may be added to cavities created in the mouthpiece 10 for positioning of microphone 40 and/or transducer 50. The polymeric materials for the mouthpiece 10 may be selected for several different mechanical and acoustical properties. For example the material can be selected to achieve a desired durometer for the mouthpiece 10. The durometer of the material may be selected to maintain the shape of the mouthpiece 10, but at the same time, reduce the bite force required for the diver to hold the mouthpiece 10 in place. Suitable lower durometer embodiments, include the range of 20 to 50, more preferably, 30 to 40. In use, such lower durometer embodiments allow the diver to keep the mouthpiece 10 in their mouth for extended periods (e.g., hours) without excessive discomfort or fatigue of their jaw muscles, particularly while speaking. The properties of the polymers used for the mouthpiece 10 can also be selected to obtain a desired amount of acoustical insulation so as to minimize the transmission of sound from transducer 50 to microphone 40 by reducing or preventing feedback between the two components.

In some embodiments, a mouthpiece 10 having a lower durometer can be achieved by two ply and/or other multi-layer configurations of the mouthpiece 10 where at least a portion of the mouthpiece 10 comprises a lower durometer tooth contacting surface layer 18 (also referred to as a liner) that fits over a higher durometer (e.g., more rigid), underlying core structure 19. The latter provides sufficient rigidity for holding the shape of the mouthpiece 10 in the diver's mouth, while the former provides a soft comfortable tooth contacting surface. Liner 18 may also be configured to provide acoustical insulation/dampening properties so as to reduce feedback between microphone 40 and transducer 50 by reducing the transmission of sound from transducer 50 and microphone 40. In use, such two ply or other multilayer embodiments of the mouthpiece 10 provide a more comfortable mouthpiece that minimizes or reduces feedback from the transducer 50 and microphone 40, while maintaining the overall shape of the mouthpiece. In related embodiments, mouthpiece 10 can have a three or even a four ply construction to provide additional amounts of acoustic insulation.

Microphone 40 is positioned in or on mouthpiece 10 and is configured to detect the sound 41 (herein voice sounds 41) from the diver's voice with the mouthpiece 10 in place and to generate an electrical output 42. Microphone 40 may comprise various miniature microphones known in the art and may comprise various electric microphones known in the art. The microphone 40 may include or be coupled to a preamplifier 47 as well as a filter device 43 for filtering out the diver's breath sounds or other non-speech related sounds (e.g., bubble and cavitation sounds). In various embodiments, filter 43 may correspond to one or more of a high pass, low pass or band pass filter. Filter 43 may also be programmable, so as to allow the user to select various acoustic criteria for filtering out breathing sounds. Such criteria may include a particular frequency range, duration of sound and/or amplitude of sound that is filtered. Filter 43 may also be configured to filter out acoustic signals 52 (discussed below) generated by acoustical transducer 50 so as to minimize feedback from transducer 50 and microphone 40. In an alternative or additional embodiment, filter 43 may also be configured as or include a switching device 43s that shuts off the generation of signals 42 by microphone 40 when the diver is receiving signal acoustic signals 52 from transducer 50. In use, such embodiments provide another approach and means for minimizing or eliminating feedback between microphone 40 and acoustic transducer 50.

In some embodiments, microphone 40 may be placed in a variety of different locations in or on the mouthpiece 10. In one or more embodiments, microphone 40 is positioned on an opposite side 22 of the mouthpiece as the side containing acoustic transducer 50 so as to minimize feedback between the microphone and acoustic transducer 50 (side 22 being defined by the divers left and right). In other embodiments, the microphone is placed on an opposite bite structure 30 from that of acoustic transducer 50. In such embodiments, bite structure 30 is configured to dampen or attenuate any vibrations coming from acoustical transducer 50. Also, microphone 40 may be placed on the surface 12 of mouthpiece 10, but is more preferably recessed within the mouthpiece so as to attenuate breath sounds as well as reduce the likelihood of exposure to liquids in the diver's mouth. In other embodiments, microphone 40 is configured and positioned to actually detect breath sounds so that the diver's respiration rate can be determined (by detecting repeating breath sounds 41) as well as other respiratory characteristics such as depth or shallowness of respiration. The latter two qualities may be determined by the duration and amplitude of output signal 42 generated by microphone 40. In some embodiments, the microphone 40 may be positioned near or at the front section of the mouthpiece 10 in order to more effectively detect a diver's breath sounds.

In one embodiment, mouthpiece 10 can include a first and a second microphone 40' and 40" where the first microphone 40' is positioned for optimizing the detection of breath sounds (e.g., in the front section 14 of the mouthpiece) and the second microphone 40" is positioned at another location on the mouthpiece where the amplitude breath sounds will be reduced or a minimum. For example, the second microphone 40" may be positioned on either side of the mouthpiece or recessed below the surface of the mouthpiece. In some embodiments, the output signal 42' from microphone 40' can be used for a two-fold purpose. First, it can be used for the detection of respiration rates and other respiratory characteristics (e.g., tidal volume, depth of respiration, etc.). Second, it can also be used to attenuate the noise or interference from the diver's breaths sounds on the diver's voice sounds by subtracting all or a selected portion of output signal 42' from output signal 42" (e.g., noise cancellation). Other signal processing operations on output signal 42" using output signal 42' are also contemplated (e.g., averaging, use of first order, second order equations, Laplace transformations, etc.). In this way, microphones 40' and 40" can allow a single mouthpiece 10 to be used for both voice communication and for sensing and communicating biometric data such as respiration characteristics.

In some embodiments where the mouthpiece 10 has a recessed microphone 40, the mouthpiece 10 can include a cavity 44 in which the microphone 40 is placed. The cavity may include a small aperture 45 or opening to the mouthpiece surface 12 to allow for acoustical conduction to the mouthpiece 10. The diameter of aperture 45 can be selected to minimize the entry of fluids into the cavity, and in various embodiments, can be in the range of 0.001 to 0.00001 inches (0.00254 to 2.54e-005 centimeter), more preferably, 0.0005 to 0.0008 inches (0.00127 to 0.002032 centimeter) with a specific embodiment of 0.0007 inches (0.001778 centimeter). One or both of aperture 45 and microphone 40 may include a waterproof layer 46, which may correspond to a porous material such as an expanded PTFE material. In other embodiments, the microphone 40 may also be potted or positioned within cavity 44 with a sound insulating material, such as one or more curable polymers having sound insulating properties (e.g., silicone). In use, such embodiments having a potted microphone 40 provide a means for reducing feedback between microphone 40 and acoustic transducer 50 as well as dampening of other unwanted sounds (e.g., from the diver clenching his jaw on the mouthpiece), which may be conducted through mouthpiece 10.

An acoustic transducer 50 is positioned on the upper surface 33 of at least one of the left or right bite structure 30. The acoustic transducer 50 is configured to transduce an electrical signal input 51 (encoding or corresponding to an acoustic signal) received by the diver's communication device 100 into an acoustic output signal 52. Input signal 51 can be from one or more of another communication device 100 (either from another diver's device or from a surface ship), a dive computer, a music player (e.g., an MP3 player) or other related devices. In particular embodiments, input signal 51 can be generated and/or conditioned by a processor 170 (described herein) or other signal conditioning device or circuitry of communication device 100 or a processor 70 resident within mouthpiece 10. Processor 70 or 170 may correspond to a microprocessor and can be configured to generate and/or condition signal 51, as well as condition signal 42 from microphone 40. Such signal conditioning in either case can include one or more of amplification, filtering, conversion, matching and isolation.

Transducer 50 is also configured to acoustically couple to the diver's upper teeth UT to conduct the acoustic output 52 from the diver's upper teeth through the skull S to the cochlea in order to generate audible sound in at least one of the diver's ears E when the diver is wearing mouthpiece 10. In many embodiments, the transducer 50 comprises an acoustical plate 53 (also described as a vibrating plate 53) coupled to a driver 54. The plate 53 is configured to engage and acoustically couple to the surface of the diver's teeth and be vibrated by the driver 54 responsive to electrical signal 51. Vibration of the plate 53 produces acoustical signal output 52 which is acoustically conducted to the divers teeth and then through the bones in his or her skull to the inner ear IE, including cochlea C where they are perceived as sound. Plate 53 can be fabricated from ceramic, metal, polymeric material such as a resilient polymer, and can have a size and shape to acoustically couple to one or more of the diver's teeth. In particular embodiments, plate 53 may have a curved horizontal shape 53c corresponding in part to the curvature of the diver's dental arches DA to facilitate the plate contacting multiple teeth. Plate 53 may also have one or more ridges or other raised feature 53r configured to enhance acoustical coupling and conduction to the diver's teeth. In particular embodiments, ridges 53r can be positioned to contact the center depressions in the diver's teeth.

In particular embodiments, plate 53 can be configured to have an acoustical impedance approximating or otherwise matched in some fashion (e.g., proportional, inversely proportional, etc.) to that of the diver's teeth (e.g., one or more of the upper teeth). Such embodiments can be achieved by fabricating plate 53 from one or more dental ceramics or other material having similar properties as the diver's teeth. Other acoustic properties can also be matched, such as the resonant frequency of the plate and the teeth. Such matching of acoustic properties can be configured to minimize acoustic losses from plate 53 to the teeth or otherwise enhance conduction of acoustic signal 52 through the diver's skull to the inner ear including the cochlea.

In various embodiments, driver 54 comprises an electromagnetic driver 55, which can be directly or indirectly coupled to plate 53. In the latter embodiments, driver 54 comprises electromagnetic driver 55, a movable diaphragm 56 sitting atop or otherwise coupled to the driver 55, and a lever or other connecting means 57 coupling diaphragm 56 to plate 53. Electromagnetic driver 55 can comprise various electromagnetic drivers known in the speaker or earphone arts and can comprise a miniature magnet 58 which may correspond to a core or coil. One or more of driver 55, movable diaphragm 56, lever 57 and magnet 58 can be fabricated from mems-based components either separately or as a single structure. In alternative embodiments, driver 55 may be configured to be directly coupled to plate 53 without diaphragm 56 and/or lever 57.

typically, acoustic transducer 50, including plate 53, is positioned to engage the upper (e.g., maxillary) back teeth of the diver's mouth M, but may be positioned to engage any tooth or group of teeth in the diver's mouth, such as the front upper or lower teeth. As an addition or alternative embodiment, transducer 50 including plate 53 may also be configured to engage and be acoustically coupled to the diver's upper palate (the hard palate). In such embodiments, the plate 53 can have a curved shape matched to at least a portion shape of the upper palate (also known as the roof of the mouth). Such embodiments allow for larger surface area of acoustical conduction to the diver's skull and do not require the diver to bite down on the mouthpiece when speaking.

In various embodiments, mouth piece 10 can include a sensor 60 which is configured to detect the diver's breath and generate an output signal 61 which is used to switch off microphone 40 and/or attenuate or gate the output signal 42 coming from the microphone to communication device 100 during a time period of the diver's respiration. In the first configuration (where the microphone is switched off), the output signal 61 can be fed into microphone switching device 43s, and in the second signal 61 can be sent to communication device 100 including processor 170. In some embodiments, sensor 60 can correspond to a miniature flow/velocity sensor for detecting a flow rate and/or velocity of the diver's breath moving through the mouth. When the velocity or flow exceeds a threshold value, corresponding to flow or velocity of a diver's breath, the microphone 40 can be configured to shut off, and/or output signal 42 can be attenuated or gated by processor 170. The threshold value for flow and/or velocity can be selected so as to be able to distinguish between a velocity or flow rate when the diver is speaking or breathing, the former being lower than the latter. In various embodiments, processor 170 and/or microphone 40 may include logic for shutting of the microphone 40 and/or attenuating or gating signal 42 or 51. In specific embodiments, such logic for attenuating or gating signal 42 or 51 can be incorporated into one or more modules 190, described herein.

For embodiments where sensor 60 comprises a flow sensor, the sensor can be positioned in a variety of locations on mouthpiece 10 for detecting the diver's breath. In one embodiment, flow/velocity sensor 60 is placed toward the front section 14 of the mouthpiece 10 (e.g., near the front teeth), preferably in the center 15 of the front section 14, so as to be in a location in the diver's mouth having the greatest velocity/flow rate (for example, at the peak of a velocity profile such as a velocity profile for poiseuille flow). Such profiles can be determined using standard measurement methods known in the art for a standard mouth shape, size and tidal volume (or other related respiratory measurement), with adjustments made for a particular diver with a particular shaped mouthpiece 10.

Figure 10:
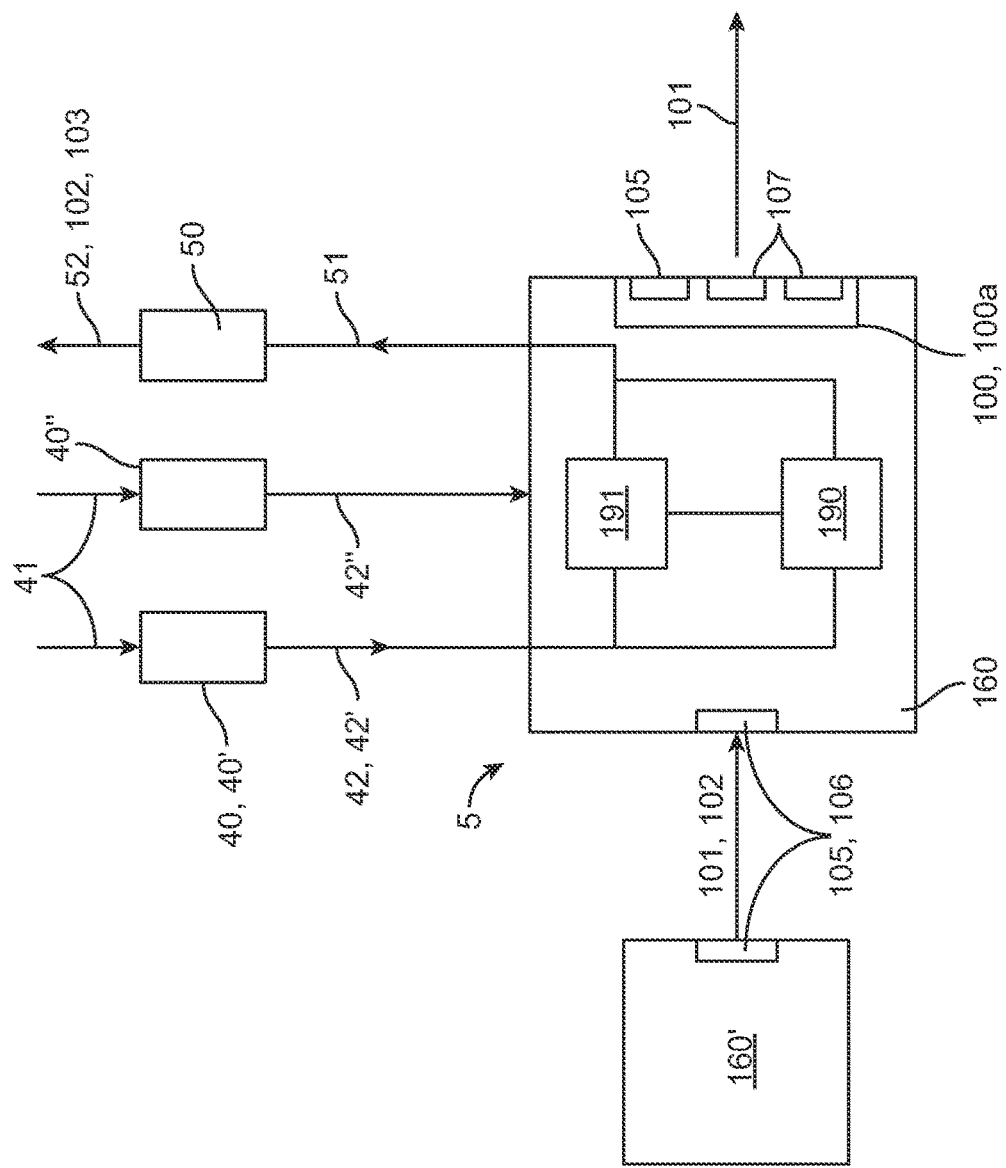
FIG. 10 is a schematic view illustrating the configuration and operation of an embodiment of the communication device for use with embodiments of the voice communication mouthpiece apparatus.

Communication device 100 can employ a variety of communication modalities including, without limitation, electromagnetic, such as RF, magnetic, optical, acoustical and/or combinations thereof. Referring now to FIG. 10, in some embodiments, the communication device 100 can correspond to an ultrasonic or other acoustical transmission device 100a which transduces the electrical output signal 42 into an acoustic signal 101, which is transmitted by the acoustical transmission device 100. In such embodiments, communication devices 100 can comprise one or more acoustical transducers 105 which transmit and/or receive acoustical energy at a selected frequency or range of frequencies. Selected frequencies can be in the range of 10 to 40 kHz, 30 to 40 kHz, 100 to 200 kHz and 150 to 200 kHz. This frequency can be adjusted for one or more of the depth, salinity and temperature conditions of the water. Acoustical transducers 105 may correspond to one or more ultrasonic transducers 106, which can comprise various piezo-electric materials, such as piezo-electric ceramic materials. The particular acoustical transducer 105 and acoustical frequency can be selected based on the desired acoustical transmission range, acoustical sensitivity, bandwidth, maximum diving depth, temperature and salinity conditions and related parameters.

Also, acoustical transducers 105 may be configured as both acoustical transmitters and receivers so as to send and receive acoustical signals. In many embodiments, transducers 105 can be arranged as an array 107 of transducers which may include a phased array formation. Array 107 can be configured to optimize one or more of the transmission range, sensitivity and bandwidth of communication device 100. In various embodiments, the frequency, power settings and sensitivities of transducers 106 and/or array 107 can be selected to enable underwater transmission ranges for communication device 100 up to 1500 feet (457.2 meters) and more preferably, up to 2500 feet (762 meters) with even great transmission ranges contemplated. Also, communication device 100 can include signal generation and selection circuitry to allow for communication over multiple selectable acoustic frequency ranges, herein after channels. Communication device 100 may also include a multiplexing device (not shown) coupled to at least one of the transceiver or signal processing circuitry so as to allow for the transmission of multiple signals. The multiplexing device may be configured for one or more of time division, frequency division or code division multiplexing. In alternative embodiments communication device 100 can comprise an RF based device and can even include RF communication chip 95 described above. In these and related embodiments, RF communication chip 95 is configured to have a selected power and frequency to enable underwater communication with other divers 210 and ship 220.

Figure 11:
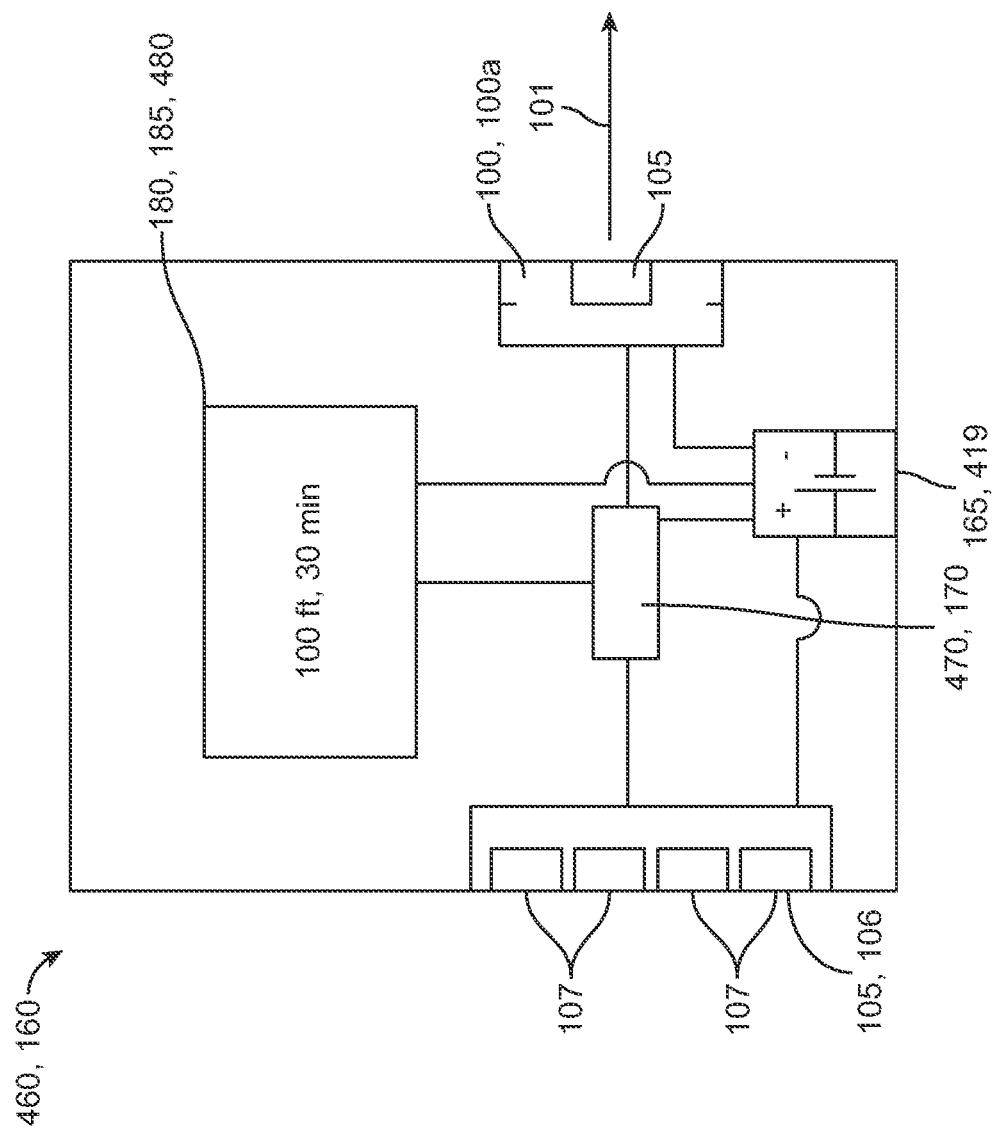
FIG. 11 is a schematic view illustrating the configuration and operation of an embodiment of a PWE device (such as a dive computer) including a communication device for use with embodiments of the voice communication mouthpiece apparatus.

Referring now to FIG. 11, in many embodiments, communication device 100 can be incorporated into a portable watertight electronic (PWE) device 160. PWE device 160 will typically comprise a PDA (Personal Digital Assistant) device 160 (or other similar devices) that is worn or carried by diver 200. PWE device 160 may also comprise or be integrated into a dive watch, dive computer or other device or equipment carried by the diver (e.g., a flash light, depth gauge, regulator, etc.). For ease of discussion, PWE device 160 will now be referred to as a dive computer 160; however, other embodiments are equally applicable. Dive Computer 160 includes a processor 170, display 180, user input means 185 and an electrical power source 165. Power source 165 may correspond to a portable battery such as a lithium or lithium ion battery or other battery chemistry known in the art. User input means 185 may correspond to a touch screen which may be separate or integral with display 180. Processor 170 includes one or more modules 190 including software programs or other logic for controlling various operations of device 160 including those of communication device 100. For example, in various embodiments, module 190 can comprise a program for distinguishing between when a diver is speaking versus when the diver is breathing by using an output 61 from sensor 60 and then gating or attenuating microphone output 42 and/or transducer output 51 accordingly.

In other embodiments, module 190 can comprise a program or other logic instruction set for generating and sending various voice commands and other voice messages 102 to the diver to alert them of various conditions, etc. and/or assist them in the performance of one or more tasks. In one embodiment, module 190 can comprise a program for enabling a controlled ascent for a diver. The program may send voice prompts to the diver telling him or her how long to remain at a particular depth before he or she can ascend to the next depth so as to avoid the bends or other related conditions. The program can be configured to send the prompts in response to one or more inputs such as those from an electronic depth gauge, electronic timer, SCUBA tank pressure or related gauge or sensor. Other inputs can include various messages from other divers 120 as well as the dive boat or other surface ships.

The processor 170 will typically correspond to one or more microprocessors known in the art and can be selected for increased durability, fault tolerance and pressure resistance for underwater operation, using various MIL-SPEC criteria known in the military/naval equipment arts. Processor 170 will typically include one or more modules or algorithms 190 for generating, conditioning and controlling signals sent to and from the mouthpiece 10, including signals 102 corresponding to voice messages as well as controlling other operations to allow two way voice communication by diver 200. Modules 190 may also be configured for computing, monitoring and communicating various physiological data of the diver, including for example, heart rate, respiration rate, blood pressure, blood oxygen saturation and other blood gas measurements (e.g., blood nitrogen). In many embodiments modules 190 are configured to calculate blood oxygen saturation or other blood gas saturation using output from optical detector 413 and oxymetry methods known in the art. Module 190 can also include algorithms to calculate the divers pulse rate based on variations in the diver's blood oxygen saturation using methods known in the art.

Processor 170 may also include other modules 190 which use such data to determine if the diver is in a state of physiologic stress (e.g., such as stress caused by low blood oxygen levels, "hypoxia" or out gassing of nitrogen, causing the "bends," etc.) or a precursor state which precedes or is otherwise predictive of a state of physiological stress. When such a stress state or precursor state of stress is detected, it may be communicated by the first communication device 100 to a second communicative device 110 to allow other individuals (such as those on the dive boat or even those onshore) to monitor the diver(s) and alert them when it is time to ascend and/or if diver requires assistance.

In particular embodiments, PWE device 160 can comprise a dive computer 160 or a related device that is carried or worn by the diver and is configured to provide the diver various voice messages 102 (also referred to as spoken messages 102) including alerts, prompts and commands using mouthpiece 10 and acoustic transducer 50. This can be achieved through the use of processor 170, audio signal generator 176, and one or more modules 190 that are configured to generate and signal voice messages to the diver in response to one or more conditions and/or as part of a voice instruction set to the diver.

Figure 6A:
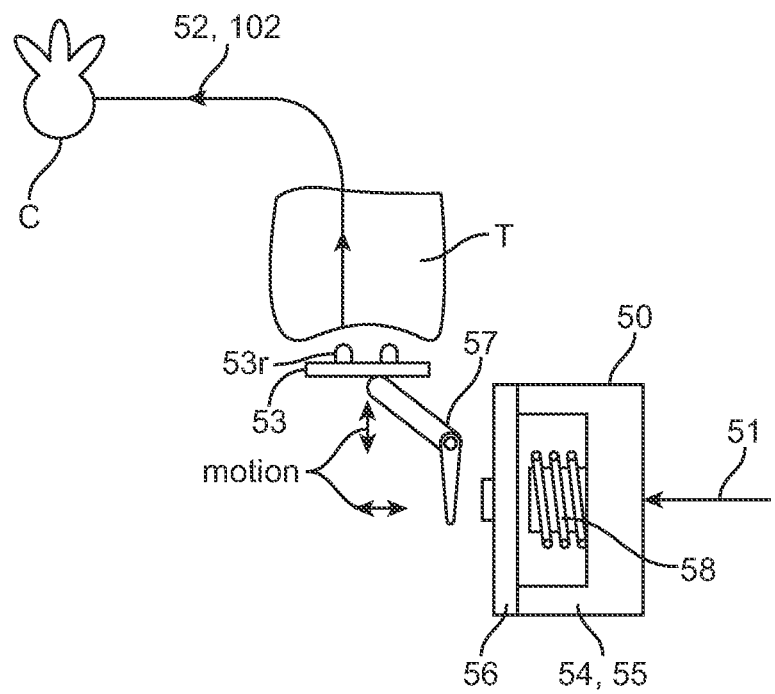
FIG. 6a is a side cut-away view showing an embodiment of the acoustic transducer comprising an electromagnetic driver, acoustical plate and connecting lever.
Figure 6B:
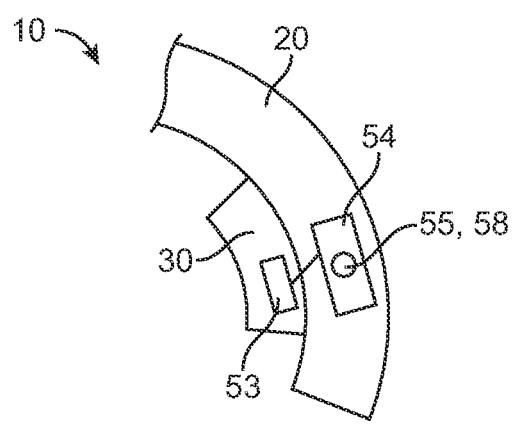
FIG. 6b is a top down view showing an embodiment of the acoustic transducer positioned in/on the mouth piece.
Figure 6C:
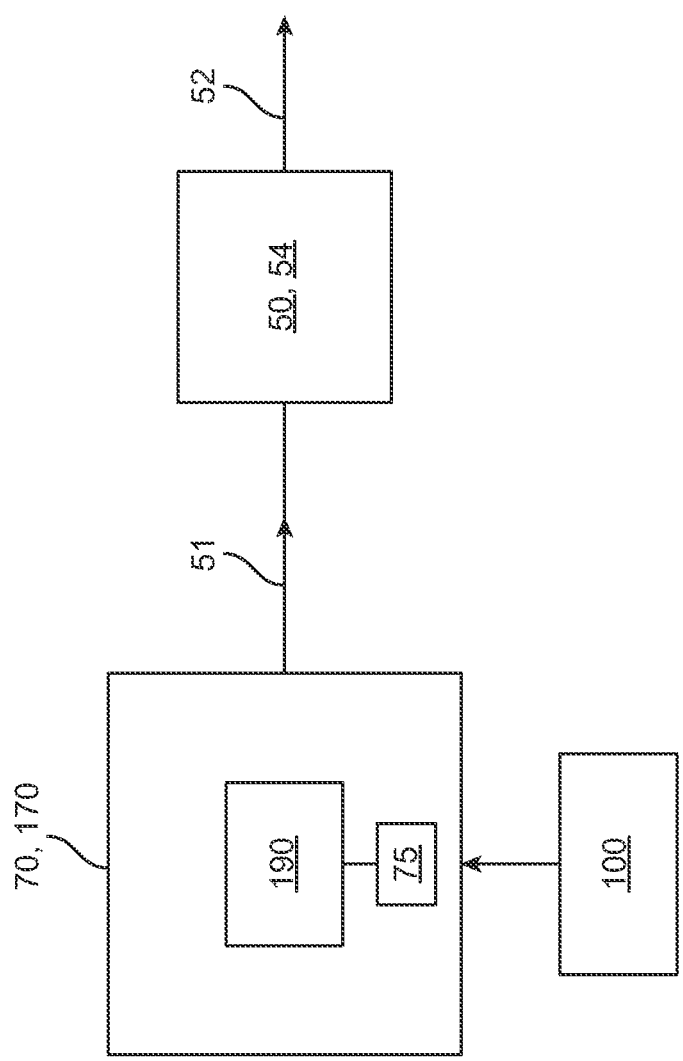
FIG. 6c is a block diagram showing the configuration and operation of an embodiment of the acoustical transducer.
Figure 6D:
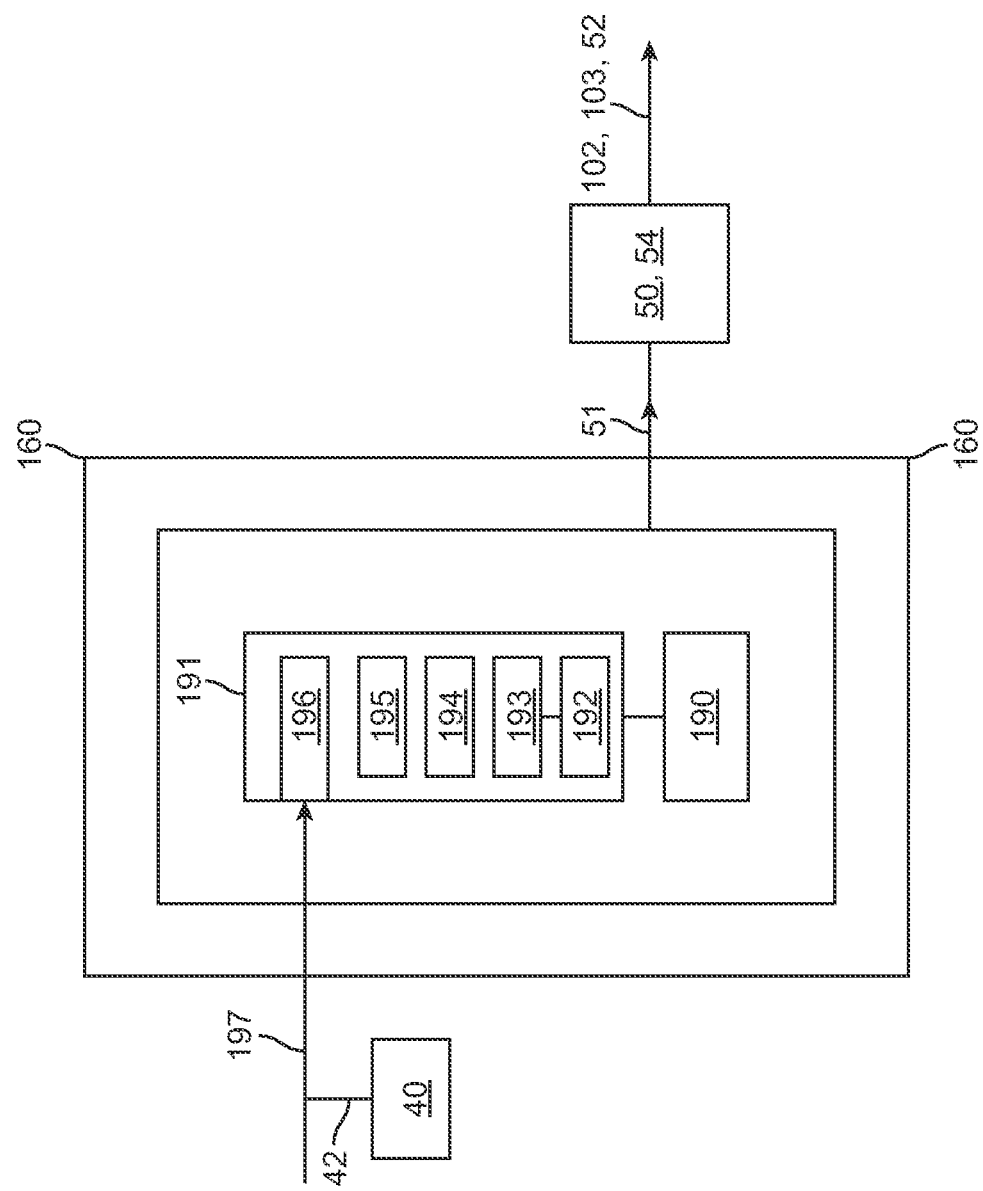
FIG. 6d is a block diagram showing the configuration and operation of an embodiment of a communication system for generating voice prompts and other messages that are delivered to the diver by embodiments of the acoustical transducer.
Figure 7B:
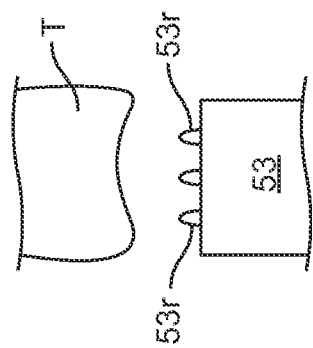
FIG. 7b is a side view illustrating an embodiment of the acoustical plate having conducting ridges.
Figure 7A:
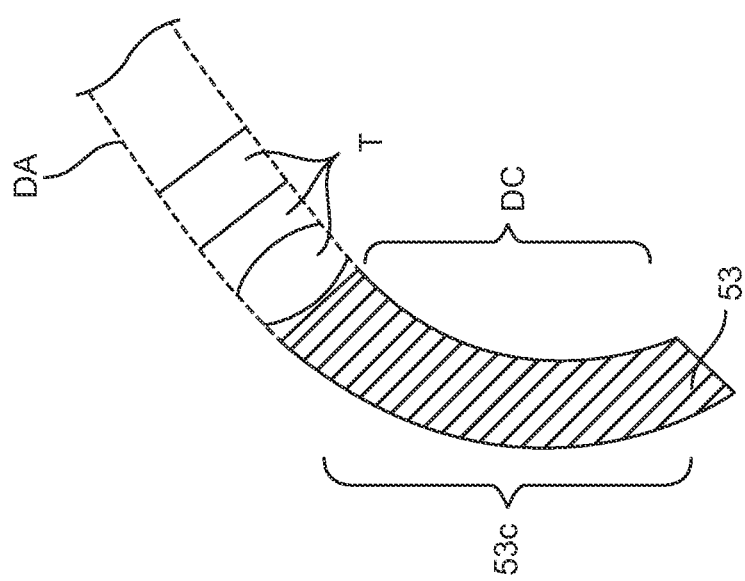
FIG. 7a is a top down view illustrating an embodiment of the acoustic plate having a curved shape corresponding to curvature of the diver's dental arches.
Figure 8:
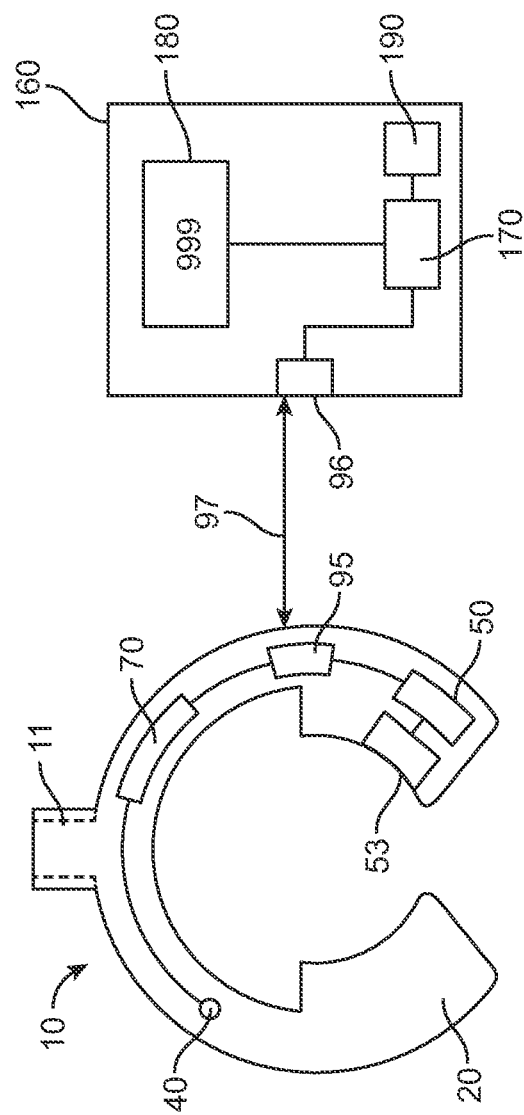
FIG. 8 illustrates an embodiment of the mouthpiece having a wireless communication device such an RF communication chip for communicating with a diver computer or other PWE device.
Figure 9A:
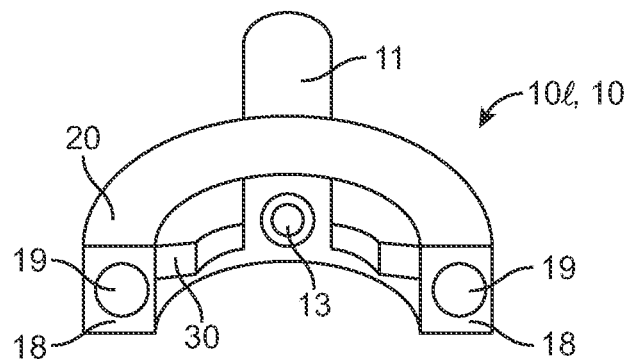
FIG. 9a is a cut away perspective view illustrating an embodiment of a multilayer mouthpiece having a rigid core and softer outer layer.
Figure 9B:
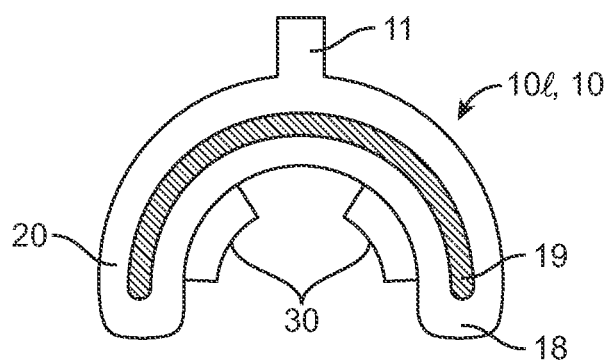
FIG. 9b is a cut away top down view illustrating an embodiment of a multilayer mouthpiece having a rigid core and softer outer layer.

Referring now to FIGS. 6d and 10, in various embodiments, modules 190 can include a speech synthesizer module 191 which generates audio signals 51 corresponding to voices messages 102. In use, such embodiments allow the diver to perform a number of tasks and activities, including various mission critical tasks without having the distraction of having to look at an instrument.

Speech synthesis module 191 can comprise various speech synthesis algorithms known in the art. Additionally in various embodiments, speech synthesis module 191 is configured to generate audio signals 52, which correspond to a selected spoken voice 103. Spoken voice 103 can include for example, the diver's own voice, or another person's voice similar that used in aircraft navigation and control systems. One or both of modules 190 and 191 can include the capability for the diver 100 to record specific messages 102 in their own voice or that of another individual to allow module 191 to output those messages to the diver 100 or another diver 110. Further, modules 190 and 191 may also include the capability for the diver to record a sufficient number of vocalizations (in their own voice or that of another individual) to allow module 191 to generate any spoken message 102 and not just those spoken by the diver or other individual. The techniques for generating voices 103 from such vocalizations can include various algorithms known in the speech synthesis arts, for example, various concatenation routines 192 using stored speech units 193 derived from the speaker's (e.g., the divers) vocalizations. Such routines can be embedded within the programming of module 191 or they may be external.

In an additional or alternative embodiment, modules 190 and 191 can also include the ability for the diver to fine tune the voice 103 to have selected acoustic properties (e.g., pitch, volume, etc. to their liking). Such voice selection capability can be achieved by the use of one or more algorithms incorporated into module 191 such as a pitch variation algorithm 194, rate variation algorithm 195 (and other adjustment algorithms known in the speech synthesis arts), which adjust audio signals 51 to produce the desired voice 103. In use, such embodiments allow the diver to select a voice that they are most comfortable with and can mostly easily hear, particularly underwater. In the latter case, device 160 and modules 190, and 191 can include the capability to allow the diver to fine tune voice 103 while they are underwater with the mouthpiece 10 in place. Accordingly, in various embodiments device 160 can include various user input devices or other means 185 (e.g., knobs, touch screens, etc.) for making such adjustments.

In addition to manual adjustment of voice 103, in various embodiments device 160 can also include means for varying the acoustical characteristics of voice 103 depending upon variations in one or more conditions experienced by the divers so as to maintain the diver's ability to hear messages 102 spoken by voice 103. Such conditions can include ambient noise levels, the diver's depth, water pressure and other like conditions. Accordingly modules 191 can include one or more control algorithms 196 (e.g., PI, PID, etc.) which operate using an input 197. In various embodiments, input 197 may comprise one or more of depth, pressure, ambient noise, etc. For the case of ambient noise levels, the input 197 can comprise signals 42 from microphone 42 or microphones coupled to device 160. In use, such embodiments allow the diver to continue to hear commands 102 from voice 103 during changes in their depth and in ambient noise levels (e.g., from a passing boat) which may otherwise drown out or reduce the acoustic fidelity of the voice 103. Module 191 can also adjust voice 103 as well depending on the particular type of SCUBA 80, mask and mouthpiece used by the diver to account for variations in acoustical conduction and other acoustical characteristics.

Modules 191 can also be configured to modulate or otherwise adjust voice 103 to account for reduced levels of conduction by bone at higher acoustic frequencies. This can be accomplished, for example, through the use of pitch variations routines 195 which shifts the pitch of all or a portion of the frequency components of voice 103 to lower frequencies (e.g., make voice 103 sound deeper). In other embodiments, conduction through the bone of the higher frequency components of voice message 102 or other acoustic signals 52 may also be improved by using high pass signal routines implemented in hardware (e.g., a high pass filter coupled to op amp device) or in software by a module 198 running on one or both of processor 170 and 70. Such an approach (either in hardware or software) amplifies the higher frequency components of voice 103 or other acoustic signal 52 by a selected gain which can vary depending upon the frequency (e.g., more gain for higher frequencies). In one embodiment, the amount of the gain can be determined by doing sound conduction readings through the diver's skull and/or taking bone density readings using one or more bone densitometer instruments known in the art.

Device 160 can send signals 51 to mouthpiece 10 using a variety of modalities. For example, in various embodiments, device 160 can send audio signals 51 containing modulated or otherwise encoded voice messages 102 to mouthpiece 10 via wires 17, or alternatively may do so wireless using an RF other wireless communication device 96. In another embodiment, a second device 160' that is not directly coupled to mouthpiece 10 can be used to acoustically signal voice messages 102 to device 160 which is operatively coupled to mouthpiece 10 either via wires 17 or through use of RF communication devices 95 and 96.

As described above, various embodiments, which generate spoken messages 102 (for example, using device 160), allow the diver to perform a number of tasks and activities, including various mission critical tasks without being distracted by having to look at gauge or other instruments. Further, messages 102 can include not just data such as depth, remaining air, etc., but can include prompts for performing one or more operations or tasks. For example, in one or more embodiments, messages 102 can include spoken directions for reaching a desired location, such as a dive site, or the location of a dive boat or that of other divers. Specific commands in such embodiments can include without limitation, "swim up," "swim down," "bear to the right," "bear to the left," etc. This allows the diver to navigate to such locations while looking at their surroundings and/or when there is minimal lighting.

In one or more exemplary embodiments, dive computer 160 and communication system 5 can be configured to provide the diver with voice messages 102 in the form of prompts for making a controlled ascent to the surface so as to avoid the bends. Specifically, the dive computer 160 may provide voice prompts directing the diver with various instructions, such as how long to remain at a particular depth during the ascent, what depth he or she is at, how long he or she has been at the depth, and how soon before he or she can ascend to the next depth. The computer 160 may also provide the diver with voice updates, which provide information such as the diver's ascent rate or whether they need to stay longer or shorter at a particular depth depending on various conditions. In addition to prompts and updates, the dive computer 160 may also provide voice instructions of the entire ascent plan in advance of the actual ascent in order to allow the diver to get a sense of the entire plan.

While in many embodiments, mouthpiece 10 is configured for use with a SCUBA 80, in other embodiments, the mouthpiece can also be configured for used with a snorkel or like apparatus, allowing a snorkeler to have two way voice communication with another snorkeler, diver 210 or ship 220. In such embodiments, the entire system 5, including communication device 100 can be contained in the mouthpiece 10. Further, in such embodiments, the connecting portion 11 can be sized and shaped to detachably connect to a standard sized snorkel, allowing the diver to attach the mouthpiece 10 to an off the shelf commercial snorkel and have a skin diving version of underwater communication system 5. In other embodiments, mouthpiece 10 and system 5 can be adapted for use with virtually any breathing apparatus, such as those used by fire and mine rescue personnel, so as to allow two way voice communications with such apparatus.

Figure 12:
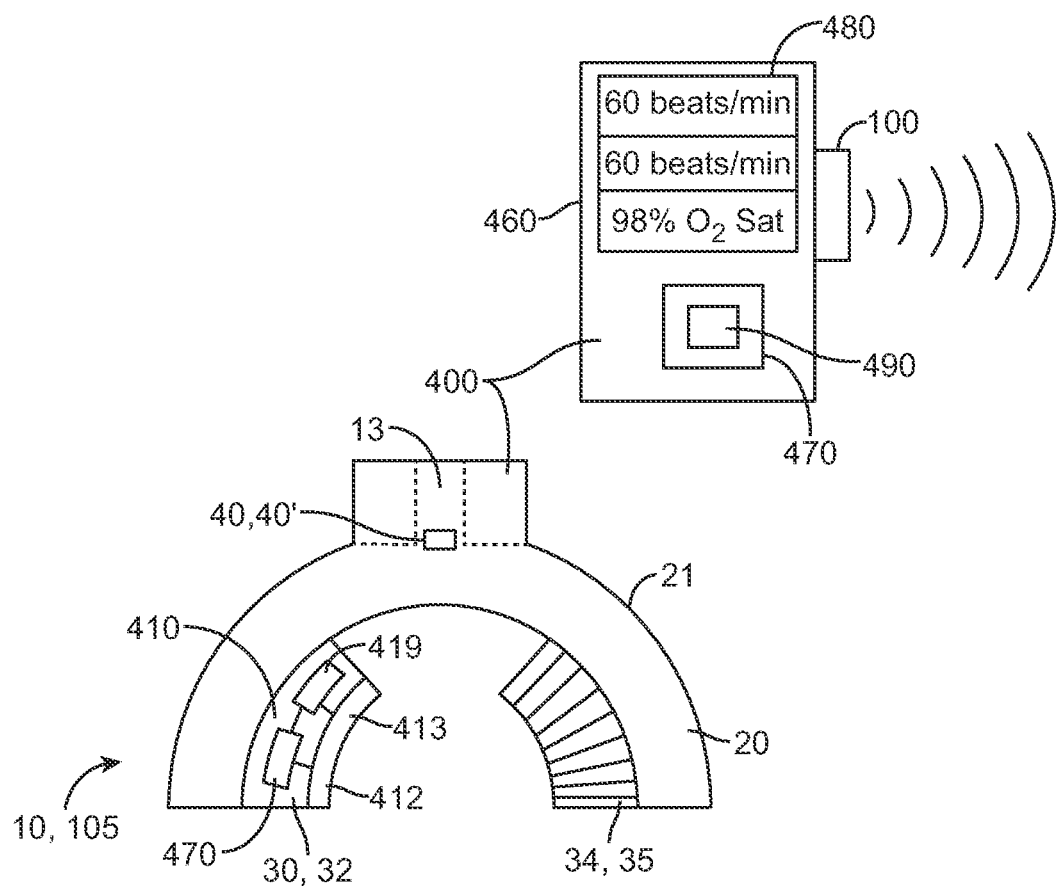
FIG. 12 is a lateral view of an embodiment of a system for measuring and communicating biometric data of a diver.

Referring now to FIGS. 12-19, various embodiments of mouthpiece 10 can also include a measurement device 410 (also described herein as sensor device 410) and methods for measuring various biometric data of a diver, such as blood oxygen saturation or that of another gas (e.g., nitrogen). Such measurements can then be converted into an acoustic signal for transmission to an acoustical communication device, such as communication device 100, described herein. Collectively, sensor device 410, mouthpiece 10 and one or more of communication device 100 (or other communication device described herein) and a monitoring device 460 may comprise a system 400 for measuring and communicating biometric data about a diver as is shown in the embodiment of FIG. 12. In these and related embodiments, mouthpiece 10 comprises a support 10s in or on which sensor device 410 is placed or otherwise disposed. Other supports 10s are also contemplated which fit into the mouth of the diver and may, for example, be configured to be retained between the diver's cheek and gum so as to be in optical contact with one or both of these types of oral tissue. Monitoring device 460 can be one in the same as device 160 and may include a display 480, which may be the same as display 180 of a communication device 100 as described herein. System 400 may also include a power supply 419 and a processor 470. The processor 470 may be one in the same as processor 70 or processor 170 for embodiments using a monitoring device 460/160. Processor 470 can include one or more modules 490 for calculating blood oxygen saturation (or other blood gas saturation, e.g., nitrogen) based on input from sensor device 410 and using absorbance equations known in the art. The module 490 can also be used to generate and control various aspects of sensor 410 including both input and outputs from the sensor. For example, in embodiments where sensor device 410 includes an optical emitter 412 and detector 413 module 490 may include various algorithms for adjusting or calibrating the optical output of emitter 412 for variations in one or more of water temperature, depth or other dive condition, variations in the location of the emitter and detector in mouthpiece 10 as well as the particular type of optical measurement (e.g., absorbance vs. reflectance for oximetry embodiments of system 400). Further, the module 490 may include algorithms to adjust the output of emitter 412 and/or that of detector 413 for motion artifact or other optical interference from movement of the mouthpiece e.g., due to movement diver's mouth and/or breathing. Module 490 may also include algorithms for calculating the diver's a pulse rate based on variations in the diver's blood oxygen saturation.

Figure 13:
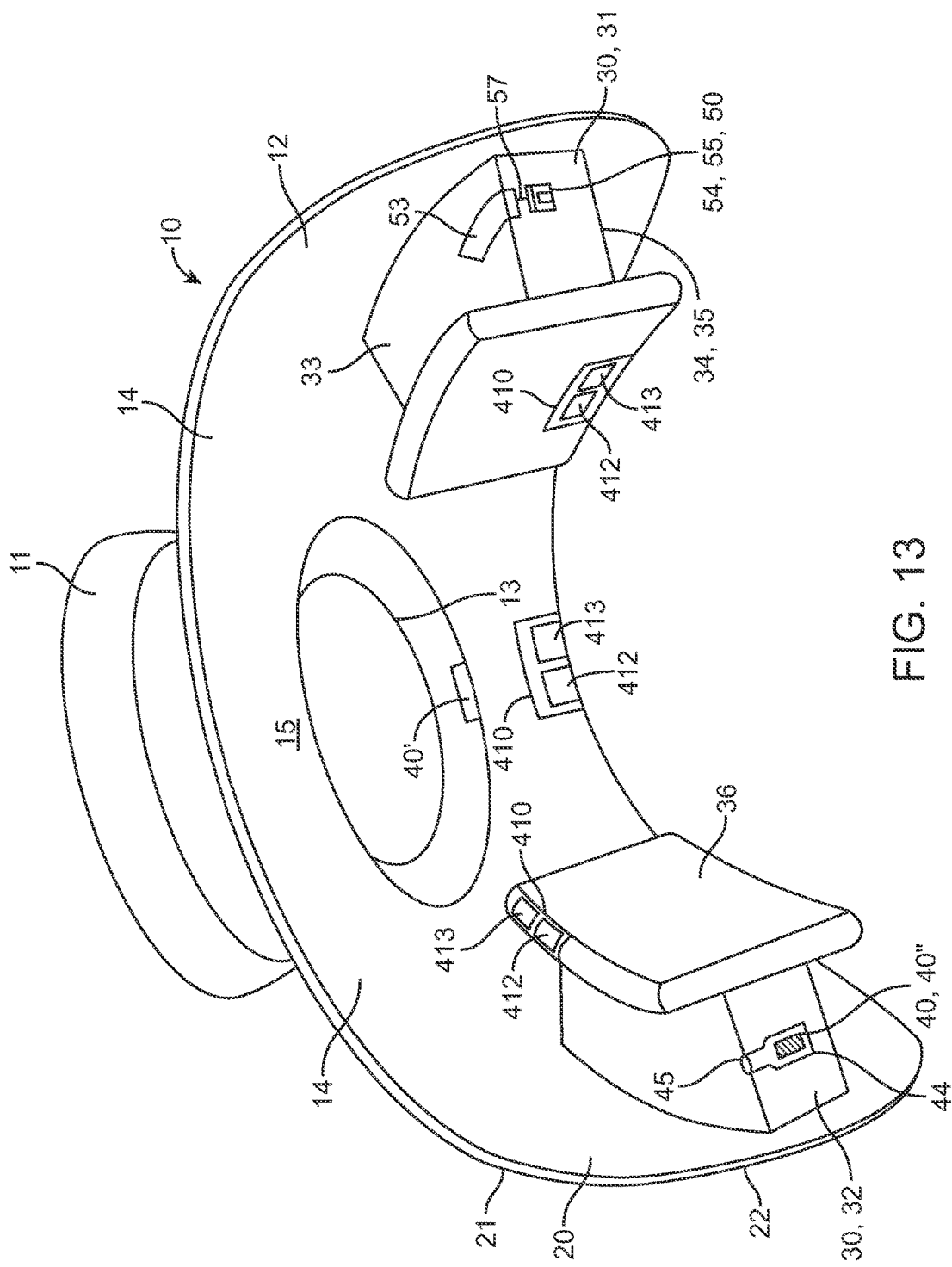
FIG. 13 is a perspective view of an embodiment of the mouthpiece including a sensor device having one or more emitters and detectors for optically measuring a blood gas saturation of a diver such as blood oxygen saturation.
Figure 14:
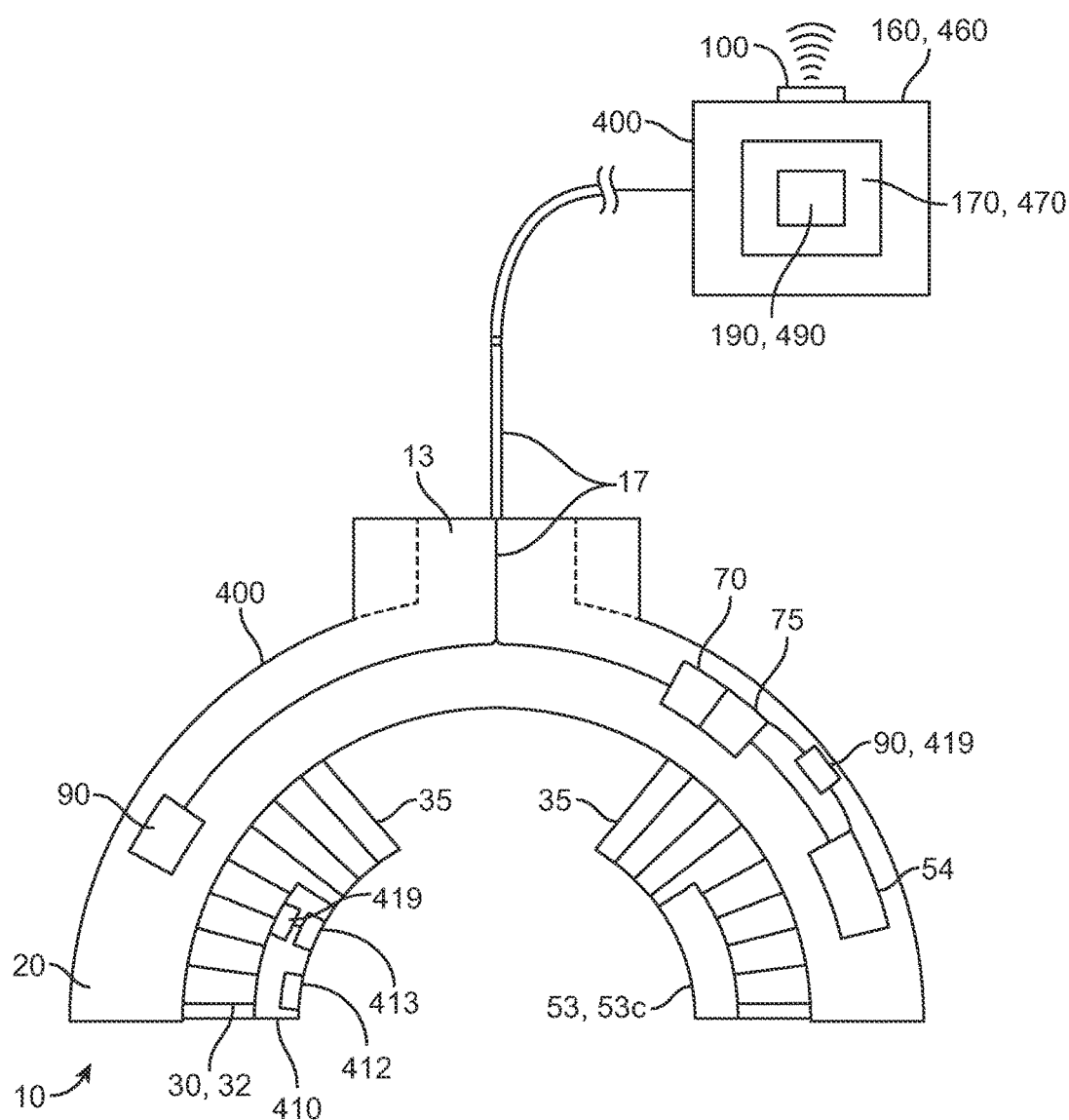
FIG. 14 is a top down view of an embodiment of the mouthpiece including a sensor having one or more emitters and detectors for optically measuring blood oxygen or other blood gas of a diver.

In one or more embodiments of mouthpiece 10 having a system 400 for measurement of biometric data, the system may include an optical or other sensor 410 for measurement of the diver's blood gases. Embodiments of a mouthpiece 10 having a sensor device 410 for making blood gas measurements are shown in FIGS. 13 and 14. In these and related embodiments, sensor device 410 includes an optical emitter 412 and optical detector 413 that are selected and arranged to emit and detect light which having an absorbance or other optical property which is correlative to a blood gas saturation such as, oxygen, nitrogen, carbon dioxide, etc. Emitter 412 may correspond to one more LED's of the same or different wavelengths, though other optical emitters are also contemplated such as lasers. Detector 413 may correspond to one or more photodiodes, phototransistor, CCDs or like devices In some embodiments, the emitter and detector of sensor device 410 are configured for measurement of blood oxygen saturation using oximetry methods. In various embodiments employing oximetry methods, adjustments can be made for the highly vascularized nature of the oral tissue OT such as buccal or gum tissue. Such adjustments can include, for example, reduction in the light intensities used for emitter 412 since the incident beam does not have to penetrate as much tissue as normal skin before encountering blood contained in the vascularized tissue within oral tissue OT. Typically, vascularized tissue or oral tissue OT lacks pigment so that it is fairly translucent relative to normal skin. Reductions in intensity in the range of 5% to 90%, with specific embodiments of 10%, 20%, 30%, 40% and 50%, relative to external skin oximetry measurements may be employed. Adjustments may also be made for reflection of light from tooth enamel underlying gum tissue. Sensor device 410 may employ wavelengths not absorbed by oxyhemoglobin or hemoglobin so as to account for reflection occurring from the tooth enamel. Reduced intensities may be employed, relative to typical reflectance oximetry, due to the reflectance from tooth enamel. Reductions in intensity in the range of 5% to 50%, with specific embodiments of 10%, 20%, 30% and 40% relative to external skin oximetry measurements may be employed. Alternatively, increased intensities may be employed.

Emitter 412 and detector 413 are positioned in the mouthpiece 10 to emit light onto the diver's oral tissue OT, which can include either the gums or the inner cheek (i.e., buccal tissue), and then to sense light that is transmitted or reflected by the oral tissue as result of the emitted light. The emitter and detector 412 and 413 may be waterproofed and configured to withstand the pressures of the dive, e.g., withstand the pressure at depths of 200 to 300 feet (60.96 to 91.44 meters). This can be achieved through the use of various mill spec/marine quality components known in the art. The sensor device 410 can also include its own electrical power source 419, such as a lithium button battery or other miniature battery known in the art, or power may be supplied from an external source.

The emitter and detector 412 and 413 can have a number of arrangements and configurations within mouthpiece 10 to achieve various objectives, for example to maintain substantial physical and/or optical contact with the diver's oral tissue OT. In various embodiments, they may be placed on the surface 12 of the mouthpiece 10 or embedded within the mouthpiece either directly or by being placed in a cavity and then potted over. In the latter two cases, the mouthpiece and/or potting material are translucent (at least to the selected wavelengths) to allow light to be transmitted through the mouthpiece to reach the diver's oral tissue and then be transmitted back. In use, such embodiments allow the conformable surface of the mouthpiece 10 or other support 10s to establish and maintain substantial physical and/or optical contact (e.g., of emitter 412 and detector 413) with the diver's oral tissue, including for example, when the diver is breathing through the piece or otherwise moving the mouth piece in their mouth. As used herein, the terms "substantial physical" and/or "substantial optical contact" means either that greater than about 75% of the area of the mouthpiece including the emitter and detector is continuously in physical and/or optical contact with the divers oral tissue, more preferably greater than 90% of said area and still more preferably greater than about 95% of said area;

and/or ii) said area is in physical and/or optical contact with the diver's oral tissue more than about 51% of the time when the diver has the mouthpiece in their mouth, more preferably, greater than about 75% of the time, still more preferably, greater than about 95% of the time. Such embodiments reduce the likelihood of an air bubble, liquid or both from optically obscuring or interfering with light going to or from emitter 412 or detector 413 so that there is no substantial effect on the measurement of blood oxygen saturation or other blood gas saturation. As used herein in the context of blood oxygen or other blood gas saturation measurement, the term "no substantial effect" or without substantial effect" means an effect of preferably less than 10%, more preferably less than 5% and still more preferably less than 2.5% with even lower amounts contemplated (e.g., less than 1%). Maintenance of substantial physical and/or optical contact emitter 412 or detector 413 may also be enhanced through the use of conformable materials for all or a portion of mouthpiece 10 so that mouthpiece can: i) conform to the contour of the contacted oral tissue OT; and ii) bend and flex with movement of the diver's mouth and/or mouthpiece to maintain said contact. In particular embodiments the section(s) of the mouthpiece 10 containing emitter 412 and/or detector 413 (e.g., flange 36) can be fabricated from materials more conformable than the remainder of mouthpiece 10.

In other embodiments for achieving substantial physical and/or optical contact with divers oral tissue, the emitter and detector may be placed on the surface 12 of the mouthpiece 10 so as to make direct contact with the diver's oral tissue. In such embodiments, the surfaces of one or both of the emitter 412 and detector 413 are desirably coated with a waterproof material and the housings for one or both can be made from conformable polymers so as to conform to the contour of the contacted oral tissue OT. In some embodiments, the emitter 412 and detector 413 may be recessed below the surface of the mouthpiece 10 a selected amount while still having direct exposure to the inside of the diver's mouth. In these and related embodiments, the emitter 412 and detector 413 may also be angled a selected amount toward the surface of the target oral tissue with the angle chosen depending upon various factors such as where the sensor device 410 is positioned on the mouthpiece (e.g., front or back of the mouth) and/or the wavelengths selected and/or the desired accuracy and precision. In various embodiments, the angle can be in the range of 1 to 90 degrees with particular embodiments of 15, 30, 45 and 60 degrees.

In other embodiments, multiple emitters and detectors 412 and 413 can be used for sensor 410 and may be arranged in a distributed pattern or array on or beneath the surface 12 of mouthpiece 10. Such an arrayed pattern provides for improved accuracy and precision of the oximetry measurement because the measurement is being made at multiple locations within the divers mouth so as to average out of any anomalous measurements due to, for example, motion artifact (e.g., of the diver's mouth or the mouthpiece) and/or sections of the diver's mouth being temporarily compressed against the mouthpiece and thus having reduced blood.

Figure 15:
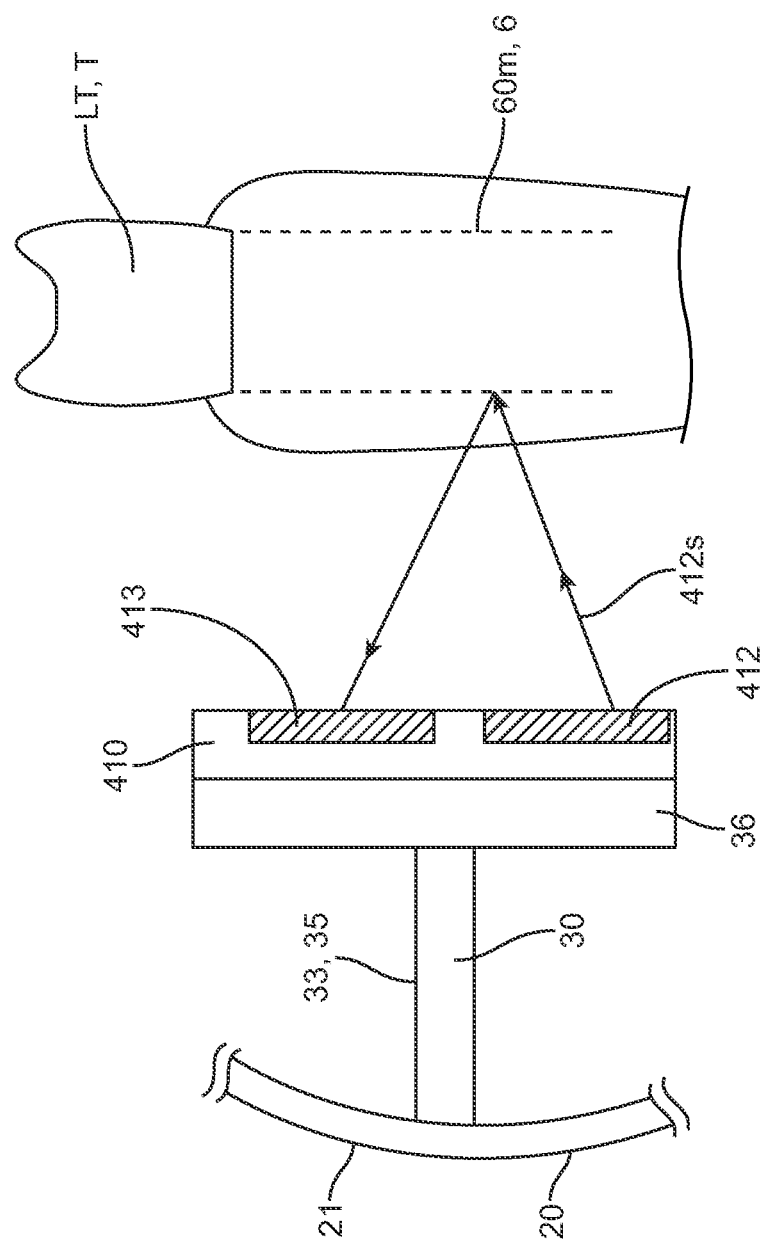
FIG. 15 is a lateral view of an embodiment of the sensor device for measuring blood oxygen using reflectance oximetry.

In addition to the various configurations described above, the emitter 412 and detector 413 may also be arranged and configured depending upon the particular type of method employed for measurement of the desired blood gas (e.g., reflectance or transmittance type oximetry for measurement of blood oxygen levels). For example, if sensor device 410 uses reflectance type oximetry, the emitter(s) and detector(s) may be placed proximate with each other on the same side of the mouthpiece 10 (whether embedded, recessed or on the surfaces), as shown in the embodiment of FIG. 15. In such embodiments, the detector 413 is detecting emitted light which is reflected from the diver's oral tissue. Also, for reflectance type embodiments, the emitter 412 and detector 413 can be positioned to make measurement for either gum G, or buccal tissue. For gum measurements, the emitter 412 and detector 413 can be positioned on the inside surface of the mouthpiece, while for buccal measurements, they can be positioned on the outside surface. Also, for buccal measurements, the intensity and wavelengths of the emitted light can be adjusted to account for reflectance of light off of the enamel of the tooth below the gum line, GL. For, example, the intensity of the emitted light can be reduced due to the increased reflectance of light off of the tooth enamel (which for normal skin would not occur resulting in a greater degree of absorbance by the deeper layers in the skin). In use, such embodiments can reduce the power requirement for making oximetry measurements and thus prolong battery life.

Figure 16:
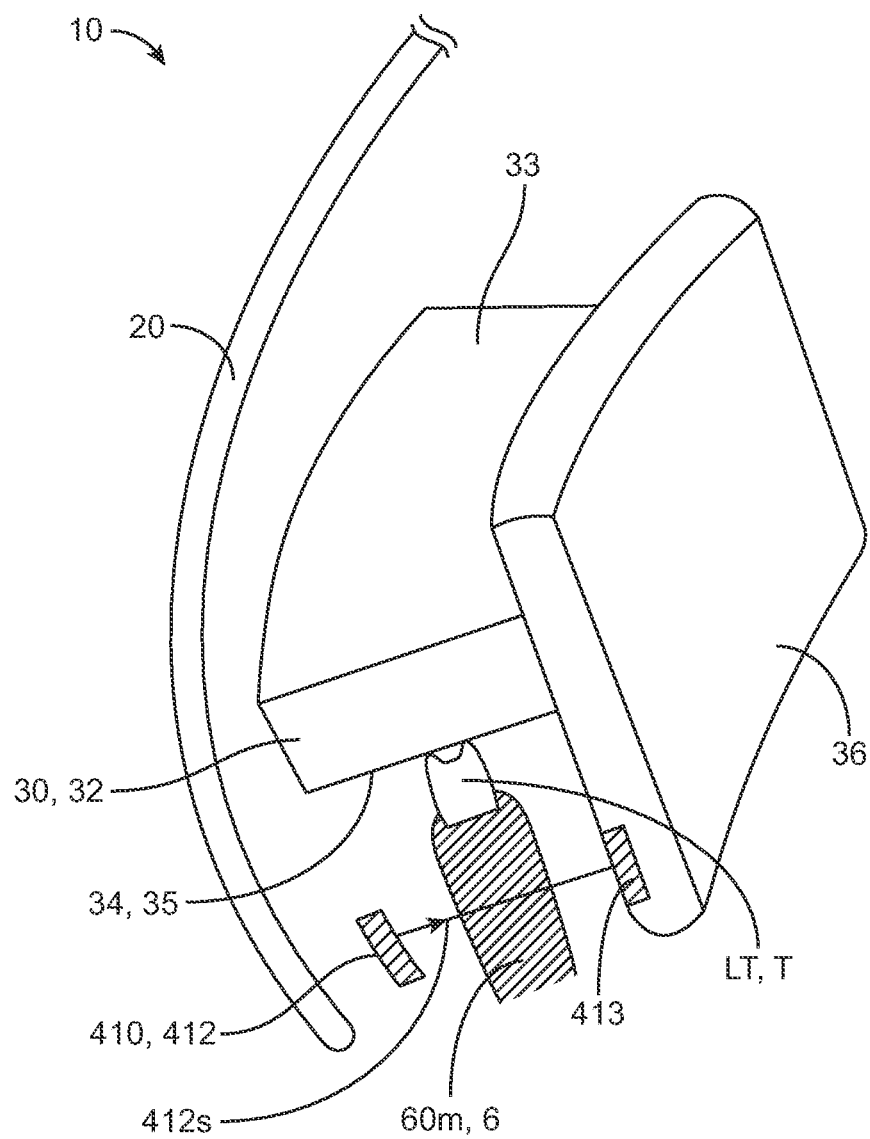
FIG. 16 is a lateral view of an embodiment of the sensor device for measuring blood oxygen using absorbance oximetry.
Figure 17:
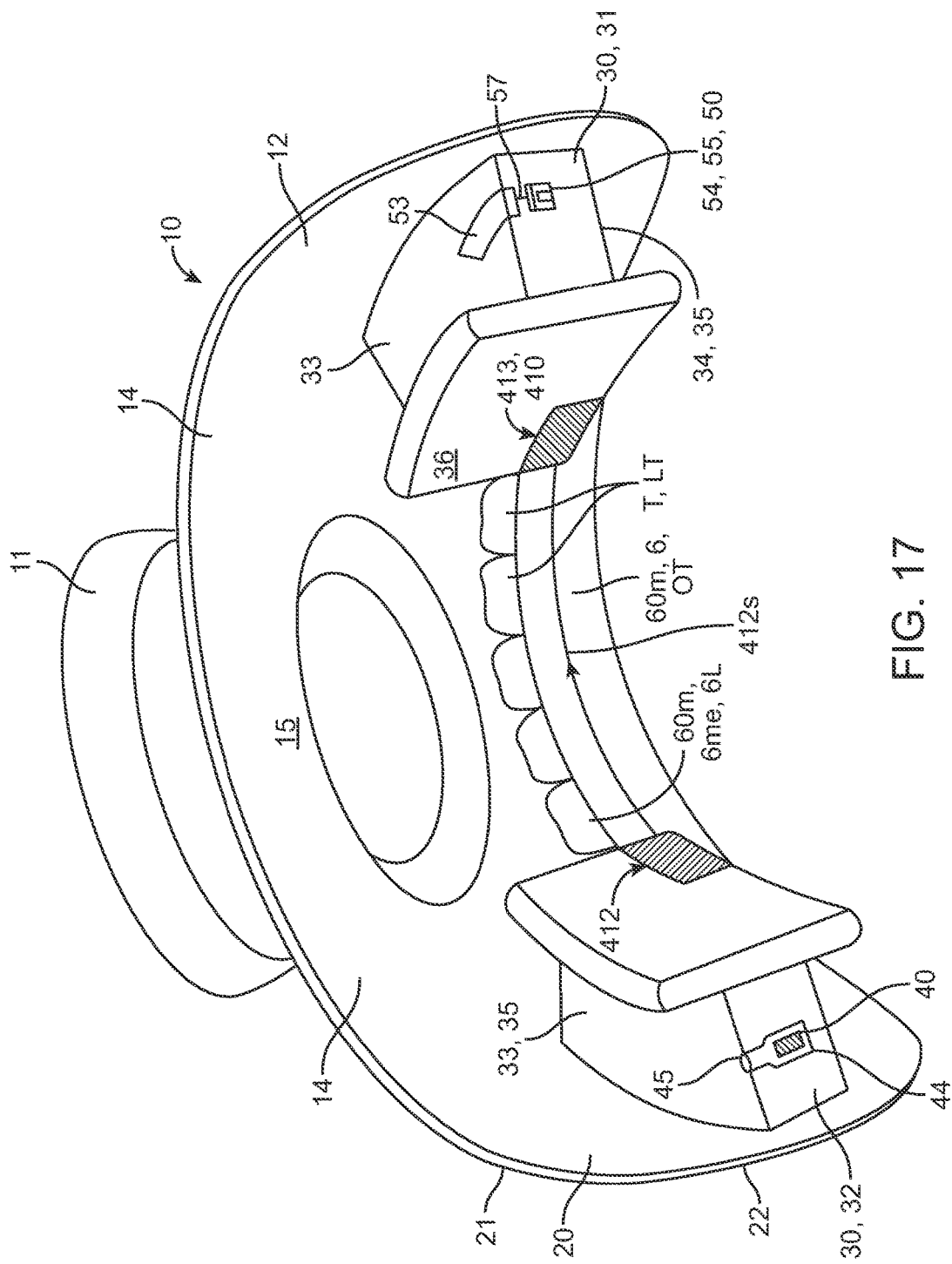
FIG. 17 is a lateral view of an embodiment of a mouthpiece including a sensor device for measuring blood oxygen using absorbance oximetry where the emitter and detector are positioned on opposite sides of the mouthpiece and below the gum line for transmittance of light through the gum tissue.
Figure 18:
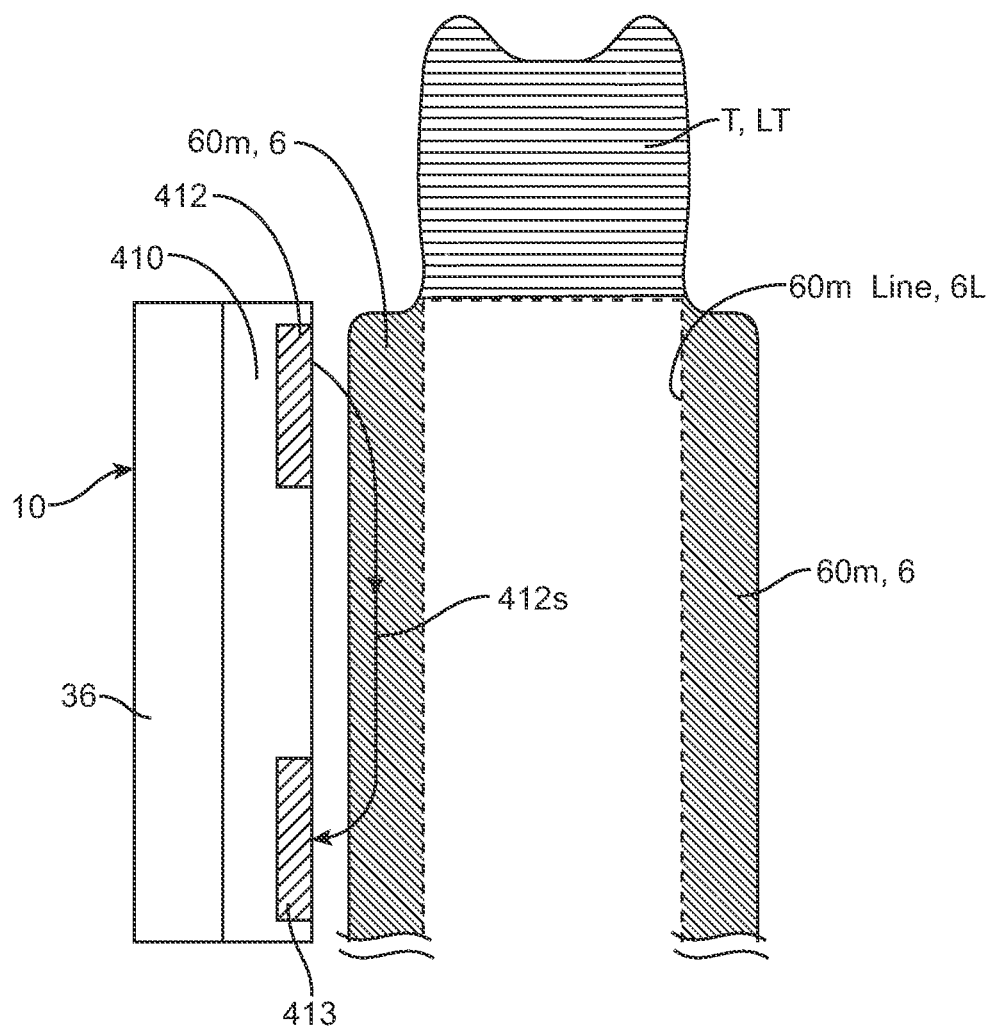
FIG. 18 is a lateral view of an embodiment of a mouthpiece including a sensor device for measuring blood oxygen using absorbance oximetry where the emitter and detector are positioned on the same side of the mouthpiece and below the gum line for transmittance of light through the gum tissue.

For embodiments using transmittance-type oximetry, the emitter 412 and detector 413 will typically be placed on opposite sides of the mouthpiece 10, as is shown in the embodiment of FIG. 16. However, several different embodiments are contemplated using absorbance type oximetry where the emitter 412 and detector 413 need not necessarily be on opposite sides of the mouthpiece. In an embodiment shown in FIG. 17, the emitter 412 and detector 413 are positioned on opposite sides of mouthpiece 10 and are further positioned to be below the diver's gum line GL such that light is transmitted through the divers gum tissue (e.g., light is transmitted from one side of the gum to the other). Sufficient intensity can be used to allow for transmission of light through gaps below the gum portion of diver's teeth. Multiple emitters and detectors can be used to accomplish this as well. In another embodiment shown in FIG. 18, the emitter 412 and detector 413 can be positioned on the same side of the mouthpiece, but at different vertical positions. The different vertical positions can be selected to allow for the transmittance of the emitted light from a location just below the gum line of the lower teeth (a location several mm's or more lower where the light is being transmitted through the layer of gum tissue covering the tooth (teeth)) with concurrent absorbance by oxygenated blood within this tissue layer.

In yet another embodiment shown in FIGS. 19a-19c, mouthpiece 10 can include flaps 38 which project between the tongue Tg and the lower palate LP, allowing for emitter 412 and detector 413 to be positioned on either side of the tongue so that light transmittance and absorbance can occur through the tissue at the base of the tongue Tg, known as the Lingual Frenulum, LF. This is a desirable area to make oximetry measurements, particularly for a diver since this area is highly vascularized and less likely to experience vasoconstriction (e.g., due to the diver's exposure to colder water), which may reduce the amount of blood contained in the tissue to be sampled.

In various embodiments, the intensity and other optical characteristics of the light emitted by emitter 412 can be modulated or otherwise adjusted for various underwater conditions, such as depth, water temperature, or optical property of the water the diver is in (e.g., turbidity, etc.) so as to maintain the accuracy and precision of the blood gas saturation measurement and/or otherwise reduce error, variation or signal noise caused in whole or part by the underwater condition. For example, the intensity can be modulated with respect to the diver's depth (e.g., by means of an electronic depth gauge that is operatively coupled to device 410 and/or PDA 460). The modulation or other adjustment can be done by logic circuitry coupled to emitter 412 and/or device 410 and/or a processor such as processor 70, 170 or 470 operatively coupled to emitter 412 and/or device 410. Higher intensities can be used for deeper depths due to fact that the higher water pressures at deeper depths may cause blood that is normally present in the upper layers of the skin to be forced away from the skin surface into deeper tissue. Thus, a stronger intensity may be needed to penetrate deeper into the skin and subjacent tissue where sufficient blood is present to make an oximetry measurement. Correlations can be developed between required intensity strength and diving depth using known mathematical modeling and/or laboratory testing and models. In various embodiments, the intensity of light from emitter 412 can be adjusted linearly, logarithmically or other manner with respect to depth (e.g., in a first, second order or other manner). A similar situation may occur for colder water temperatures, where due to vasoconstriction of the skin from colder temperatures, blood is shunted away from the skin, requiring higher intensities. Also, higher intensities can be used to compensate for losses in intensity of the incident or reflected/transmitted light from the skin due to the presence of water in the diver's mouth and various particulate matter in the water (e.g., due to scattering, reflectance etc.). In this latter case, a calibration signal may be sent to compensate for the presence of water, e.g., before emitter 412 emits an optical signal 412s used for measurement of blood oxygen saturation. Alternatively, a dual beam approach can be used for optical signal 412s with one beam directed at the diver's skin the other into any water near the diver's skin.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments of mouthpiece 10 and system 5 can be adapted for salt and fresh water environments, as well as deep dives (e.g., 60 to 200 meters (196.9 to 656.2 feet)) and cold water environments. Also various embodiments of mouthpiece 10 and system 400 can be adapted for other blood gases besides oxygen, such as nitrogen, $CO_2$, etc.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A mouthpiece apparatus for outputting biometric data of a diver, the mouthpiece comprising:
   a flexible mouthpiece configured to be worn in the mouth of the diver, comprising:
   a processor configured to control an intensity of emitted light;
   a light emitter positioned to emit light onto an oral tissue surface completely inside the mouth of the diver, the light being at a wavelength having an absorbance correlated with a level of a blood gas saturation, the processor configured to account for reflectance caused by an enamel surface in the mouth of the diver by controlling the intensity of emitted light and the wavelength of emitted light; and
   a light detector positioned to detect light which is received from the oral tissue and to generate an output signal correlated to the detected light, wherein the processor includes logic configured to modulate a characteristic of the emitted light in response to a diving condition to maintain an accuracy of a blood gas saturation measurement based on the output signal.

2. The mouthpiece apparatus of claim 1, wherein the blood gas saturation is oxygen saturation.

3. The mouthpiece apparatus of claim 2, wherein the wavelength includes at least a first and second wavelength.

4. The mouthpiece apparatus of claim 1, wherein the light emitter and the light detector are positioned to detect light transmitted through the oral tissue.

5. The mouthpiece apparatus of claim 1, wherein the light emitter and the light detector are positioned to detect light transmitted through a lingual frenulum portion of the tongue.

6. The mouthpiece apparatus of claim 1, wherein at least one of the light emitter or the light detector is positioned on a surface of the mouthpiece.

7. The mouthpiece apparatus of claim 1, wherein at least one of the light emitter or the light detector is recessed below a surface of the mouthpiece.

8. The mouthpiece apparatus of claim 1, wherein at least one of the light emitter or the light is embedded below a surface of the mouthpiece.

9. The mouthpiece apparatus of claim 1, wherein the mouthpiece is configured to conform to a contour of the diver's oral tissue to maintain substantial optical contact between the diver's oral tissue and the light emitter and the light detector during movement of the diver's mouth, cheek, jaw or teeth.

10. The mouthpiece apparatus of claim 9, wherein the mouthpiece is configured to maintain substantial optical contact between the diver's oral tissue and the light emitter and the light detector during said movement, without impeding the diver's respiration.

11. The mouthpiece apparatus of claim 1, wherein the processor is coupled to the light emitter and light detector, and configured for controlling a characteristic of the emitted light other than the intensity, and for receiving and converting an output signal from the detector into a blood gas saturation level.

12. The mouthpiece apparatus of claim 11, wherein the characteristic is at least one of a duration or wavelength of the emitted light.

13. The mouthpiece apparatus of claim 1, wherein the diving condition is a diving depth, water temperature, a presence of water in the diver's mouth or an optical property of the water surrounding the diver.

14. The mouthpiece apparatus of claim 1, further comprising:
   a power source for powering at least one of the light emitter or the light detector.

15. The mouthpiece apparatus of claim 1, wherein the mouthpiece is adapted for connection and use with a self-contained underwater breathing apparatus (SCUBA).

16. The mouthpiece apparatus of claim 1, wherein at least a portion of the mouthpiece comprises an elastomer, silicone or polyurethane.

17. The mouthpiece apparatus of claim 1, wherein the light emitter and the light detector comprise an array of emitters and detectors configured to increase an accuracy of a blood gas level measurement using the apparatus.

18. The mouthpiece apparatus of claim 1, further comprising:
an acoustic transducer positioned on the mouthpiece, the transducer configured to transduce an electrical signal input into an acoustic output and acoustically couple to the diver's upper teeth to conduct the acoustic output from the diver's upper teeth through the skull to generate audible sound in at least one of the diver's ears when the diver is wearing the mouthpiece.

19. A system for measuring and communicating biometric data of a diver, the system comprising:
the apparatus of claim 18; and
a portable device configured to send audio inputs to the acoustic transducer, the audio inputs corresponding to spoken messages for the diver; wherein the acoustic transducer converts the audio inputs into spoken messages which are conducted through the diver's skull and heard by the diver.

20. The system of claim 19, wherein the portable device comprises a dive computer or a dive watch.

21. A method for monitoring blood oxygen saturation levels of a diver, the method comprising:
positioning a mouthpiece in the mouth of the diver, the mouthpiece including a light emitter and a light detector;
emitting light onto an oral tissue surface completely inside the mouth of the diver, at least one frequency of the light having an absorbance correlated with a blood oxygen saturation level;
controlling the intensity of emitted light and a wavelength of emitted light to account for reflectance caused by an enamel surface in the mouth of the diver;
detecting an intensity of light received from the diver's oral tissue in response to the emitted light;
modulating a characteristic of the emitted light in response to an underwater condition to maintain an accuracy of a blood gas saturation measurement based on the detected intensity; and
determining a blood oxygen saturation of the diver utilizing the detected intensity.

22. The method of claim 21, wherein the emitter and the light detector are positioned in the mouthpiece to detect light transmitted through the diver's oral tissue.

23. The method of claim 22, wherein the emitter and the light detector are positioned in the mouthpiece to detect light transmitted through the gum tissue or the lingual frenulum portion of the tongue.

24. The method of claim 21, wherein the emitter and the light detector are positioned in the mouthpiece to detect light reflected from the oral tissue.

25. The method of claim 21, wherein the underwater condition is a depth of the diver, a water temperature or an optical property of water surrounding the diver.

26. The method of claim 21, wherein the intensity of the emitted light is modulated responsive to a presence of water in the diver's mouth.

27. The method of claim 21, wherein the mouthpiece is configured to maintain substantial optical contact between the diver's oral tissue and the emitter and the detector during movement of the diver's jaw, mouth or teeth, the method further comprising:
determining the blood oxygen saturation of the diver during movement of the diver's jaw, mouth or teeth, wherein the determination is not substantially affected by the movement.

28. The method of claim 21, wherein the mouthpiece is configured to maintain substantial optical contact between the diver's oral tissue and the emitter and the detector during a period of respiration of the diver, the method further comprising:
determining the blood oxygen saturation of the diver during the period of diver respiration wherein the determination is not substantially affected by movement of the mouthpiece or the diver's oral tissue during the period of respiration.

29. The method of claim 21, further comprising:
alerting the diver when the blood oxygen saturation is below a threshold level.

30. The method of claim 29, wherein the threshold level is about 95% saturation.

31. The method of claim 21, further comprising:
generating an acoustical signal encoding information on the blood oxygen saturation level, the acoustical signal configured to be transmitted underwater.

32. The method of claim 31, further comprising:
transmitting the acoustical signal from a first communication device proximate the diver to a second communication device.

33. A method for monitoring blood oxygen saturation levels of a diver, the method comprising:
positioning a measurement device in the mouth of the diver, the measurement device including a light emitter and a light detector positioned on a support; the measurement device configured to maintain substantial optical contact with the diver's oral tissue during movement of one or more of the diver's mouth, jaw or teeth and to do so without impeding the diver's breathing;
emitting light onto an oral tissue surface completely inside the mouth of the diver, at least one frequency of the light having an absorbance correlated with a blood oxygen saturation level;
controlling the intensity of emitted light and a wavelength of emitted light to account for reflectance caused by an enamel surface in the mouth of the diver;
detecting an intensity of light received from the diver's oral tissue in response to the emitted light;
modulating a characteristic of the emitted light in response to an underwater condition to maintain an accuracy of a blood gas saturation measurement based on the detected intensity; and
determining a blood oxygen saturation of the diver utilizing the detected intensity.

34. The method of claim 33, wherein the support comprises a flexible mouthpiece worn by the diver.

35. The method of claim 33, wherein the underwater condition is a depth of the diver, a water temperature, a presence of water in the diver's mouth or an optical property of water surrounding the diver.

* * * * *